US007417072B2

(12) United States Patent
Malter et al.

(10) Patent No.: US 7,417,072 B2
(45) Date of Patent: Aug. 26, 2008

(54) BLOCKADE OF PIN1 PREVENTS CYTOKINE PRODUCTION BY ACTIVATED IMMUNE CELLS

(75) Inventors: James S. Malter, Madison, WI (US); Stephane Esnault, Madison, WI (US); Zhong-Jian Shen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/383,127

(22) Filed: May 12, 2006

(65) Prior Publication Data

US 2006/0264359 A1 Nov. 23, 2006

Related U.S. Application Data

(60) Provisional application No. 60/680,387, filed on May 12, 2005, provisional application No. 60/680,441, filed on May 12, 2005.

(51) Int. Cl.
| | | |
|---|---|---|
| *A61K 31/12* | (2006.01) | |
| *A61K 31/122* | (2006.01) | |
| *A61P 11/06* | (2006.01) | |
| *A61P 29/00* | (2006.01) | |
| *C07C 49/00* | (2006.01) | |
| *C07C 50/00* | (2006.01) | |

(52) U.S. Cl. .................. 514/682; 514/690; 524/358; 568/37

(58) Field of Classification Search ................ None
See application file for complete search history.

(56) References Cited

U.S. PATENT DOCUMENTS

| | | | |
|---|---|---|---|
| 3,773,919 | A | 11/1973 | Boswell et al. |
| 4,946,778 | A | 8/1990 | Ladner et al. |
| 5,260,203 | A | 11/1993 | Ladner et al. |
| 5,984,088 | A | 11/1999 | Dietz et al. |

FOREIGN PATENT DOCUMENTS

| | | |
|---|---|---|
| EP | 036676 | 9/1981 |
| EP | 058481 | 8/1982 |
| EP | 088046 | 9/1983 |
| EP | 133988 | 3/1985 |
| EP | 143949 | 6/1985 |
| EP | 1402888 A1 * | 3/2004 |
| WO | 93/00829 | 8/1993 |
| WO | 94/001875 | 9/1994 |
| WO | WO 88/01649 | 3/1998 |
| WO | WO 99/07409 | 2/1999 |
| WO | WO 99/32619 | 7/1999 |
| WO | WO 00/01846 | 1/2000 |
| WO | WO 00/44895 | 8/2000 |
| WO | WO 00/44914 | 8/2000 |
| WO | WO 01/29058 | 4/2001 |
| WO | WO 01/36646 | 5/2001 |

OTHER PUBLICATIONS

Filipovic M, Cekic S, The Role of Eosinophils in Asthma, Medicine and Biology, 2001, 8(1): 6-10.*
Asthma in the Merck Index.*
Bai J, Peat JK, Berry G, Marks GB, Wookcock AJ, Questionnaire items that predict asthma and other repiratory conditions in adults, Chest, 1998, 114: 1343-1348.*
Eosinphil count-absolute from the Medical Encyclopedia.*
Joseph JD, Yeh ES, Wendson KI, Means AR, THe peptidyl-prolyl isomease Pin1, Progress in Cell Cycle Research, 2003, 5:477-457.*
Ryo A, Liou Y-C, Lu KP, Wulf G, Journal of Cell Science, 2003, 116:773-783.*
Eosinophilia in the Merck Index, Accessed Feb. 2, 2007.*
About EGID in the Apfed, Accessed Feb. 5, 2007.*
Maruyama T. Furutani M, Archaeal Peptidyl Prolyl Cis-trans Isomerase (PPIases), Frontiers in Bioscience 5, 2000, d821-836.*
Asthma in the Merck Index, Accessed Feb. 2, 2007.
Eosinophil count-absolute from the Medical Encyclopedia, Accessed Feb. 7, 2007.
Bass, 2001, "RNA interference: The short answer", *Nature* 411:428-429.
Elbashir et al., 2001, "Duplexes of 21-nucleotide RNAs mediate RNA interference in cultured mammalian cells", *Nature* 411:494-498.
Martinez et al., 2002, "Single-stranded antisense siRNAs guide target RNA cleavage in RNAi", *Cell* 110(5):563-74.
Schwarz et al., 2002, "Evidence that siRNAs function as guides, not primers, in the Drosophilia and human RNAi pathways.", *Molecular Cell* 10(3):537-48.
GenBank Accession No. NM_006221 (GenBank, NCBI).
Thompson and Ellman, 1996, "Synthesis and Applications of Small Molecule Libraries", *Chem. Rev.* 96(1):555-600.
Goodford, 1985, "A computational procedure for determining energetically favorable binding sites on biologically important macromolecules", *J. Med. Chem.* 28(7)849-857.
Miranker and Karplus, 1991, "Functionality maps of binding sites: a multiple copy simultaneous search method", *Proteins* 11(1)29-34.
Goodsell and Olsen, 1990, "Automated docking of substrates to proteins by simulated annealing", *Proteins* 8(3):195-202.
Kuntz et al., 1982, "A geometric approach to macromolecule-ligand interactions", *J. Mol. Biol.* 161(2):269-288.
Van Drie et al., 1989, "ALADDIN: an integrated tool for computer-assisted molecular design and pharmacophore recognition from geometric, steric, and substructure searching of three-dimensional molecular structures", *J. Comp-Aided Mol. Des.* 3(3):225-251.

(Continued)

*Primary Examiner*—Anish Gupta
*Assistant Examiner*—Julie Ha
(74) *Attorney, Agent, or Firm*—McDonnell Boehnen Hulbert & Berghoff

(57) ABSTRACT

The invention provides pharmaceutical compositions and methods of treating immunological disorders. The invention also provides pharmaceutical compositions and methods of inducing eosinophil apoptosis, and methods for treating eosinophil-associated disorders comprising inducing eosinophil apoptosis in an individual in need thereof.

3 Claims, 25 Drawing Sheets

OTHER PUBLICATIONS

Davie and Lawrence, 1992, "CLIX: a search algorithm for finding novel ligands capable of binding proteins of known three-dimensional structure", *Proteins* 12(1):31-41.

Rotstein and Murcko, 1993, "GroupBuild: a fragment-based method for de novo drug design", *J. Med. Chem.* 36(12):1700-1710.

Moon and Howe, 1991, "Computer design of bioactive molecules: a method for receptor-based de novo ligand design", *Proteins* 11(4):314-328.

Bohm, 1992, "The computer program LUDI: a new method for the de novo design of enzyme inhibitors", *J. Comp. Aid. Molec. Design* 6(1):61-78.

Jorgenson and Duffy, 2000, "Prediction of drug solubility from Monte Carlo simulations", *Bioorg. Med. Chem. Lett.* 10(11):1155-1158.

Nishibata and Itai, 1991, "Automatic creation of drug candidate structures based on receptor structure. Starting point for artificial lead generation.", *Tetrahedron* 47:8985.

Cohen et al., 1990, "Molecular modeling software and methods for medicinal chemistry", *J. Med Chem.* 33(3):883-394.

Navia and Murcko, 1992, "Use of structural information in drug design", *Current Opinions in Structural Biology* 2:202-210.

Jorgenson WL, Encylopedia of Computational Chemistry (P. V. R. Schleyer, ed.) Wiley & Sonstra., Athens, U.S.A. 5:3281-3285, Goodman Gilman, Rall, Nies, & Taylor, eds.), Pergaman Press.

Lam et al., 1994, "Rational design of potent, bioavailable, nonpeptide cyclic ureas as HIV protease inhibitors", *Science* 263(5145):380-4.

Wlodawer et al., 1993, "Structure-based inhibitors of HIV-1 protease", *Ann. Rev. Biochem.* 62:543-585.

Appelt, 1993, "Crystal structures of HIV-1 prtotease inhibitor complexes", *Perspectives in Drug Discovery and Design* 1:23-48.

Erickson, 1993, "Design and structure of symmetry-based inhibitors of HIV-1 protease", *Perspectives in Drug Discovery and Design* 1:109-128.

Mayer et al., 1987, "A unique geometry of the active site of angiotensin-converting enzyme consistent with structure-activity studies", *J. Comp. Aided Molec. Design* 1(1):3-16.

Dunbrack et al., 1997, "Meeting review: the Second meeting on the Critical Asssesment of Techniques for Protein Structure Prediction (CASP2), Asilomar, California, Dec. 13-16, 1996", *Folding & Design* 2(2):R27-42.

Bugg et al., 1993, "Drugs by design", *Scientific American* Dec:92-98.

West et al., 1995, "Targetign HIV-1 protease: a test of drug-design methodologies", *TIPS* 16:67-74.

Sidman et al., 1983, "Controlled release of macromolecules and pharmaceuticals from synthetic polypeptides based on glutamic acid", *Biopolymers* 22(1):547-556.

Langer et al., 1981, "Biocompatibility of polymeric delivery systems for macromolocules", *J. Biomed. Mater. Res.* 15:167-277.

Langer, 1982, "Controlled release of macromolecules", *Chem. Tech.* 12:98-105.

Eppstein et al., 1985, "Biological activity of liposome-encapsulated murine interferon gamma is mediated by a cell membrane receptor", *Proc. Natl. Acad. Sci. USA* 82(11):3688-3692.

Esnault et al., 2002, "GM-CSF regulation in eosinophils", *Arch. Immunol. Ther. Exp* (Warsz). 50(2):121-130.

Esnault and Malter 2001, "Granulocyte macrophage-colony-stimulating factor mRNA is stabilized in airway eosinophils and peripheral blood eosinophils activated by TNF-alpha plus fibronectin", *J. Immunol.* 166(7):4658-4663.

Schreiber and Crabtree, 1992, "The mechanism of action of cyclosporin A and FK506", *Immunol. Today* 13(4)136-142.

Khan et al., 2000, "Attenuation of the allergen-induced late asthmatic reaction by cyclosporin A is associated with inhibition of bronchial eosinophils, interleukin-5, granulocyte macrophage colony-stimulating factor, and eotaxin", *Am. J. Respir. Crit. Care Med.* 162(4 Pt 1):1377-1382.

Kita, H. et al. 1991, "Granulocyte/macrophage colony-stimulating factor and interleukin 3 release from human peripheral blood eosinophils and neutrophils", *J Exp Med.* 174(3):745-748.

Hennig, L. et al. 1998, "Selective inactivation of parvulin-like peptidyl-prolyl cis/trans isomerases by juglone", *Biochemistry* 37(17):5953-5960.

Esnault, S. & Malter, J. S, 2003, "Hyaluronic acid or TNF-alpha plus fibronectin triggers granulocyte macrophage-colony-stimulating factor mRNA stabilzation in eosinophils yet engages differential intracellular pathways and mRNA binding proteins", *J. Immunol.* 171(12)6780-6787.

Lu et al., 2001, "Critical role of WW domain phosphorylation in regulating phosphoserine binding activity and Pin1 function", *J. Biol. Chem.* 277(4)2381-2384.

Esnault and Malter, 2001, "Granulocyte macrophage-colony-stimulating factor mRNA is stabilized in airway eosinophils and peripheral blood eosinophils activated by TNF-alpha plus fibronectin", *J. Immunol.* 166(7):4658-4663.

Carballo et al., 2000, "Evidence that tristetrapolin is a physiological regulator of granulocyte-macrophage colony-stimulating factor messenger RNA deadenylation and stability", *Blood* 95(6):1891-899.

Fan et al., 1998, "Overexpression of HuR, a nuclear-cytoplasmic shuttling protein increases the in vivo stability of ARE-containing mRNAs", *EMBO J.* 17(12):3448-3460.

Capowski et al., 2001, "Y box-binding factor promotes eosinophil survival by stabilizing granulocyte-macrophage colony-stimulating factor mRNA", *J. Immunol.* 167(10):5970-5976.

Wilson et al., 2003, "Phosphorylation of p40AUF1 regulates binding to A + U-rich mRNA-destabilizing elements and protein-induced changes in ribonucleoprotein structure", *J. Biol. Chem.* 278(35):33039-33048.

Laroia et al., 2002, "Ubiquitin-dependent mechanism regulates rapid turnover of AU-rich cytokine mRNAs", *Proc. Natl. Acad. Sci. U. S. A.* 99(4):1842-1846.

Ciechanover, 1998, "The ubiquitin-proteasome pathway: on protein death and cell life", *EMBO J.* 17(24):7151-7160.

Bhattacharya et al., 1999, "Identification of AUF-1 ligands reveals vast diversity of early response gene mRNAs", *Nucleic Acids Res.* 27(6):1464-1472.

Sarkar et al., 2003, "Selective degradation of AU-rich mRNAs promoted by the p37 AUF1 protein isoform", *Mol. Cell. Biol.* 23(18):6685-6693.

Wilson et al. 2003, "Regulation of A + U-rich element directed mRNA turnover involving reversible phosphorylation of AUF1", *J. Biol. Chem.* 278(35):33029-33038.

Yaffe et al. 1997, "Sequence-specific and phosphorylation-dependent proline isomerization: a potential mitotic regulatory mechanism", *Science* 278(5345):1957-1960.

Sedgwick et al., 2003, "Oxidized low-density lipoprotein activates migration and degranulation of human granulocytes", *Am J Respir Cell Mol Biol.* 29(6):702-9.

Mizobuchi et al., 2004, "Comparison of surgical procedures for vascular and airway anastomoses that utilize a modified non-suture external cuff technique for experimental lung transplantation in rats", *J Heart Lung Transplant.* 23(7):889-93.

Haque et al., 2002, "Evidence for immune responses to a self-antigen in lung transplantation: role of type V collagen-specific T cells in the pathogenesis of lung allograft rejection", *J. Immunol.* 169(3):1542-1549.

Sekine et al., 1997, "Role of passenger leukocytes in allograft rejection: effect of depletion of donor alveolar macrophages on the local production of TNF-alpha, T helper 1/T helper 2 cytokines, IgG subclasses, and pathology in a rat model of lung transplantation", *J. Immunol.* 159(8):4084-4093.

Mizuta et al., 1991, "Total nonmicrosuture technique for rat lung transplantation", *J. Thorac. Cardiovasc. Surg.* 102(1):159-160.

Mizuta et al., 1989, "Simplified rat lung transplantation using a cuff technique", *J. Thorac. Cardiovasc. Surg.* 97(4):578-581.

Pierog et al., 2005, "Synergistic effect of low dose cyclosporine A and human interleukin 10 overexpression on acute rejection in rat lung allotransplantation", *Eur. J. Cardiothorac. Surg.* 27(6):1030-1035.

Anderson P et al., "Pin1: a praline isomerase that makes you wheeze ?", 2005, Nature Immunology 6(12):1211-1212.

* cited by examiner

Figure 1
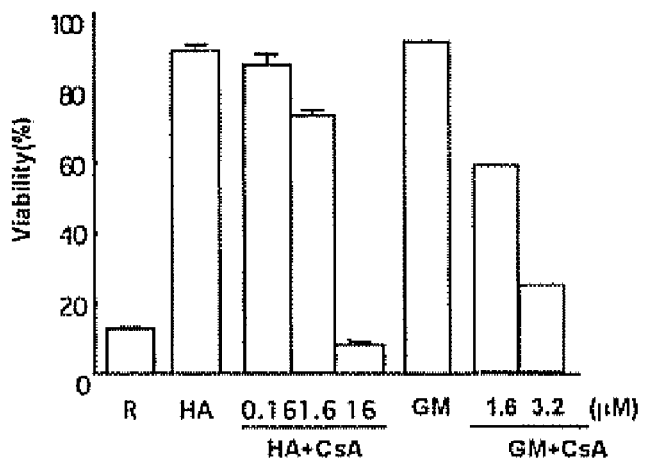
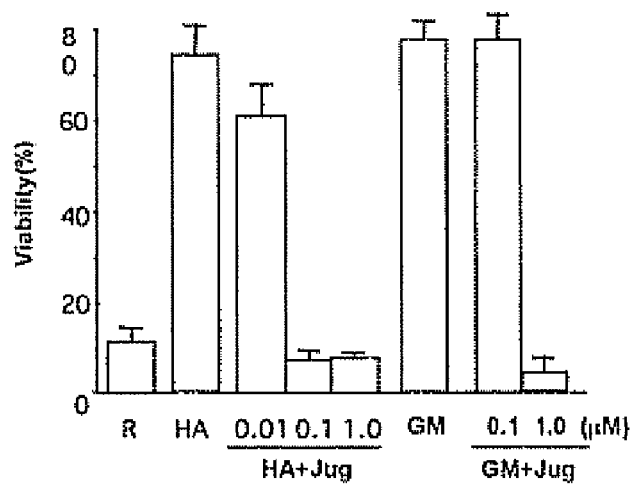
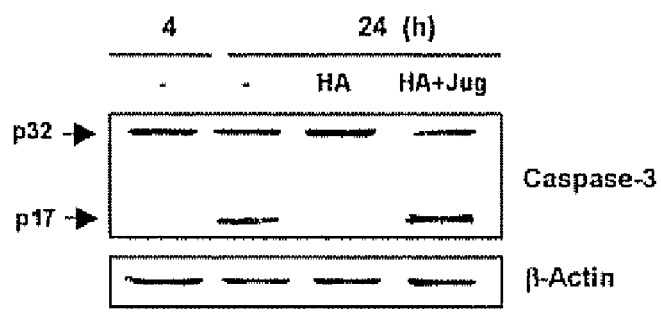

Figure 2
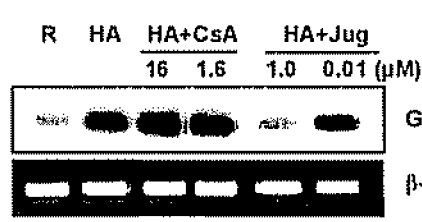
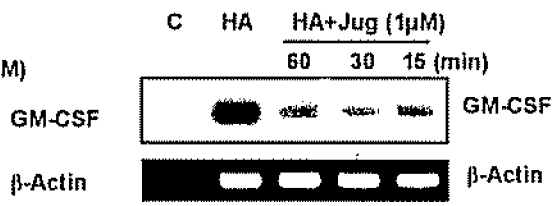
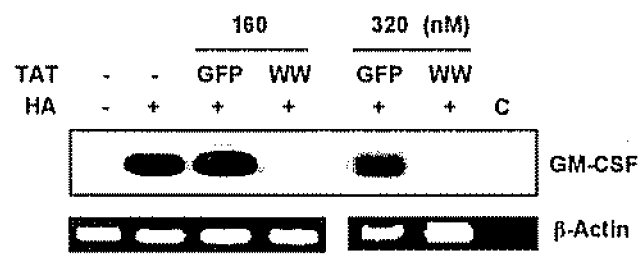
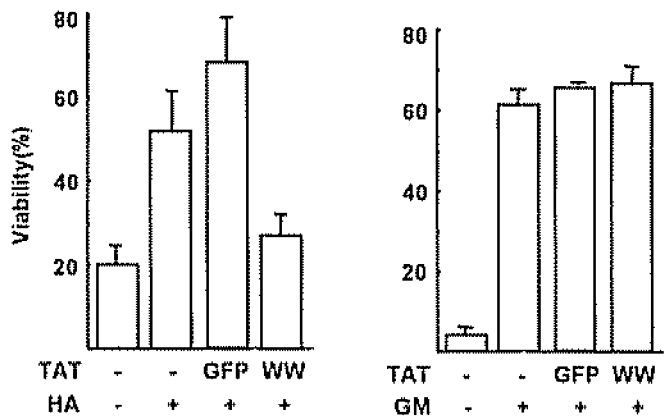
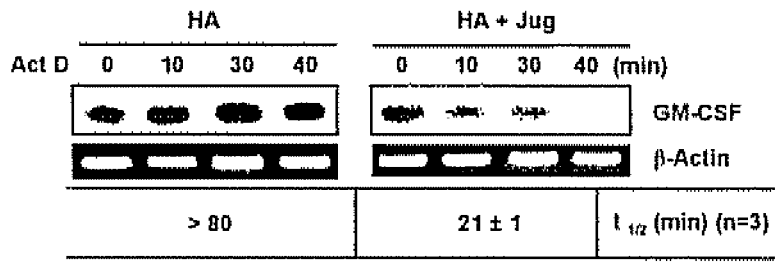

Figure 3
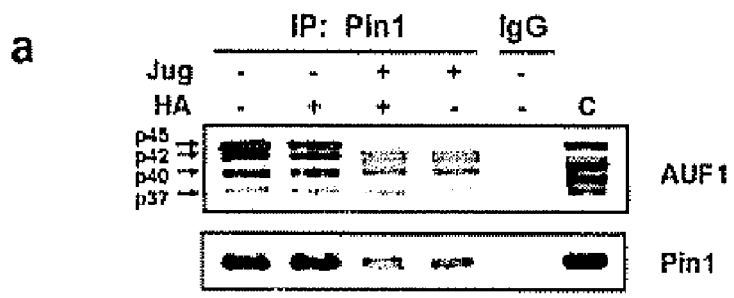
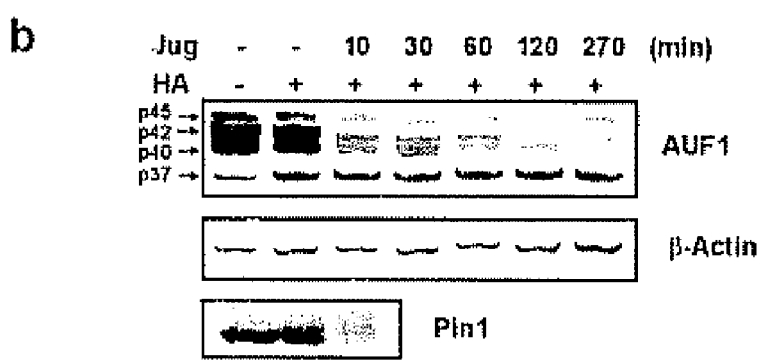
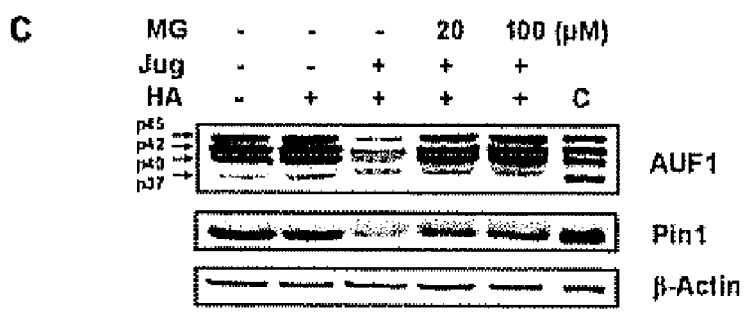
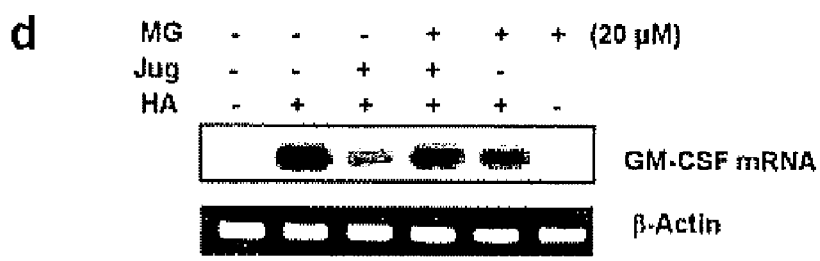

Fig. 6

| AREBP | Pin1 site | IP |
|---|---|---|
| AUF1 | Yes | ++ |
| hnRNP C | No | - |
| HuR | Yes | ± |
| KSRP | Yes | - |
| Nucleolin | Yes | - |
| PMScl75 | Yes | - |
| TIA-1 | Yes | - |
| TIAR | Yes | - |
| TTP | Yes | - |
| YB-1 | No | - |

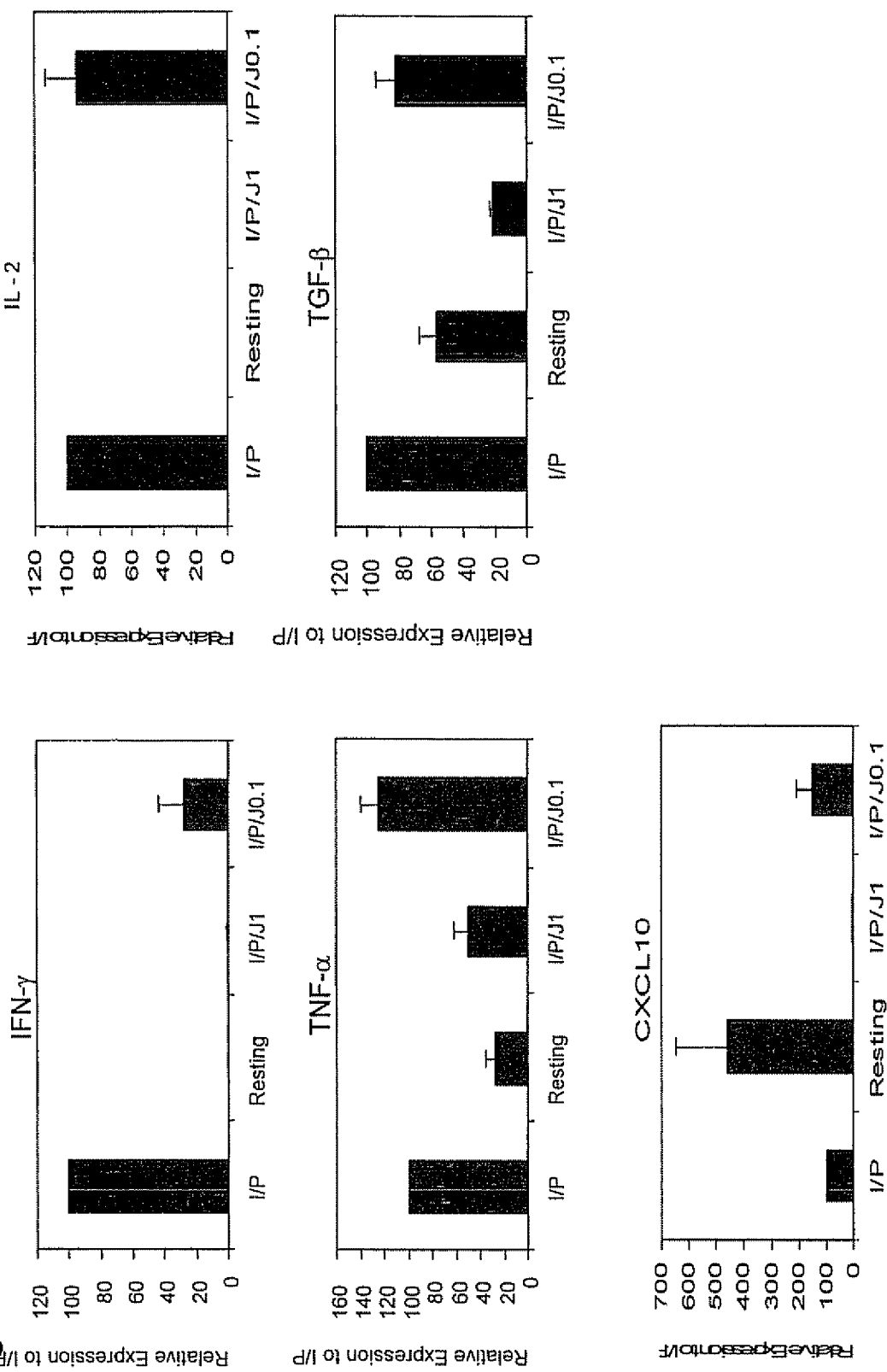

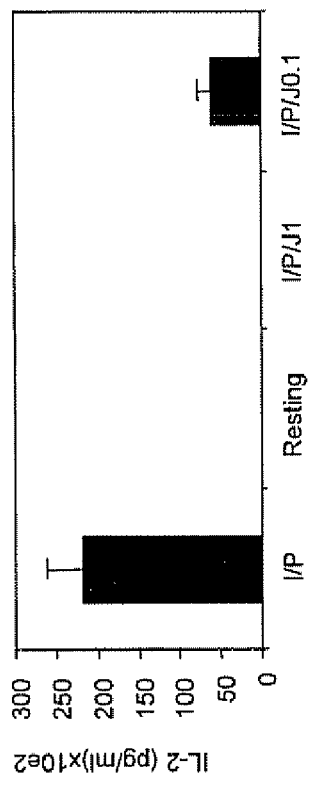
Fig. 14B
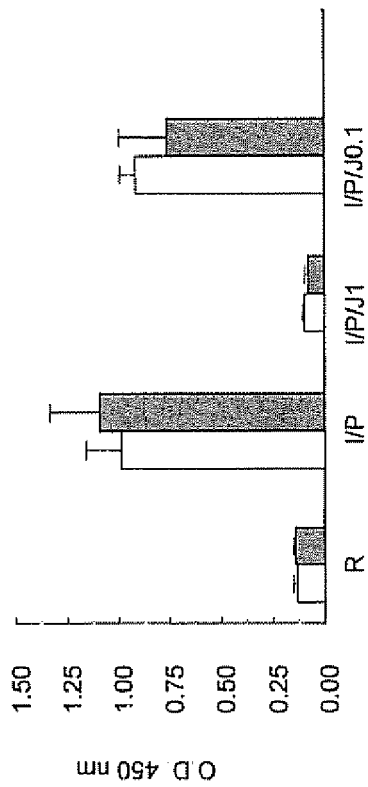
Fig. 14D
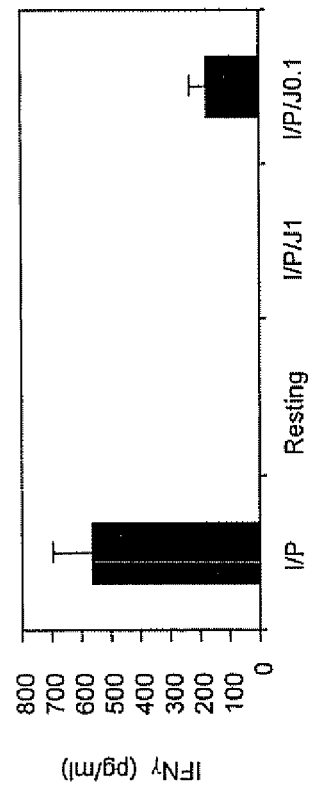
Fig. 14C
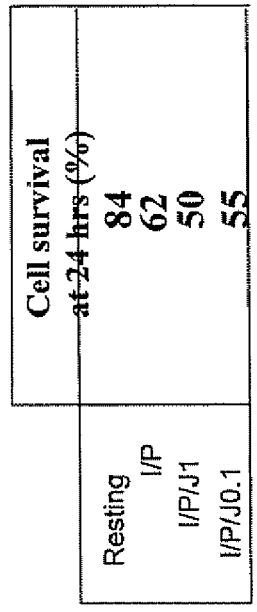

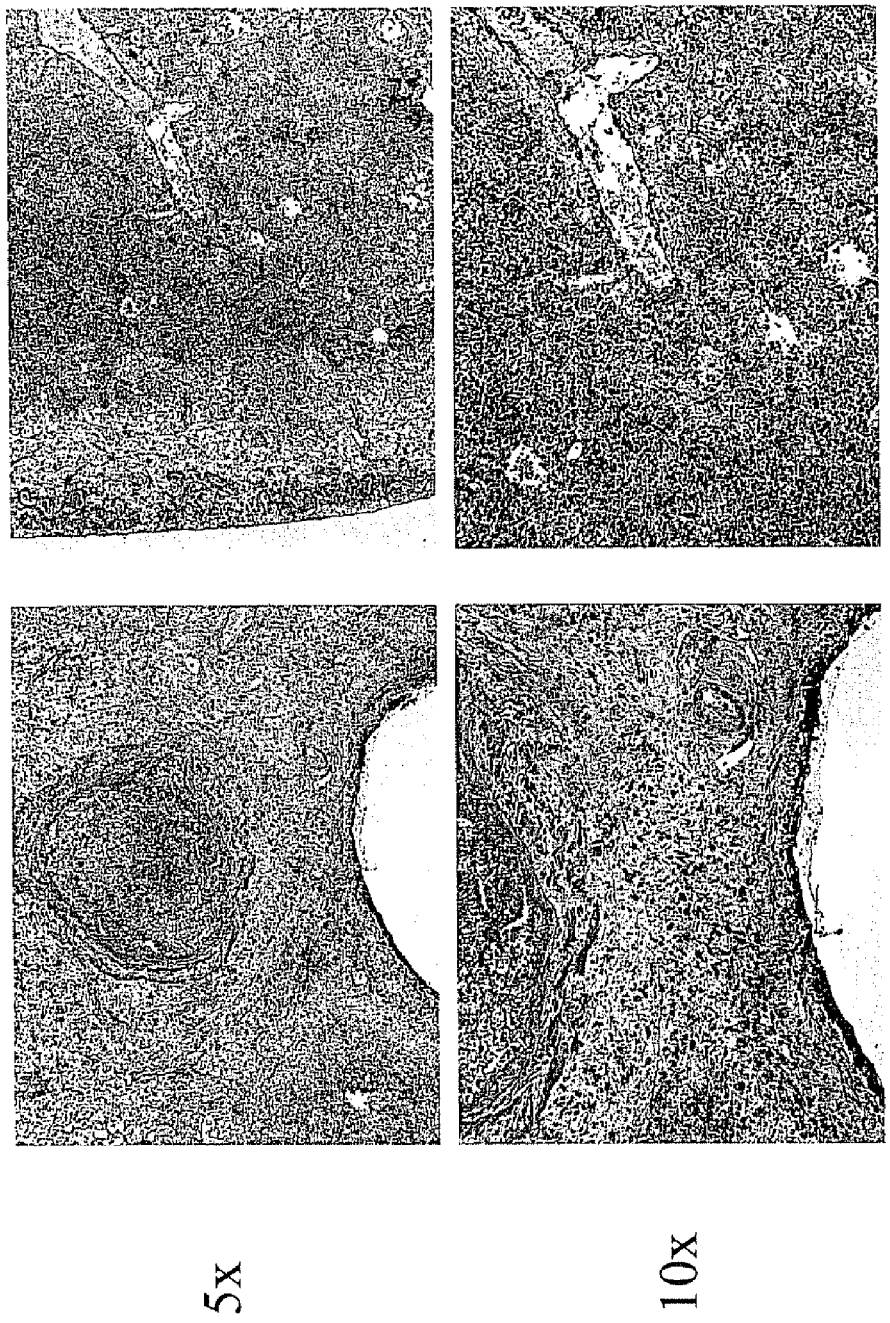
Fig 15 Control allogenic tx day 8 after transplantation-Fig

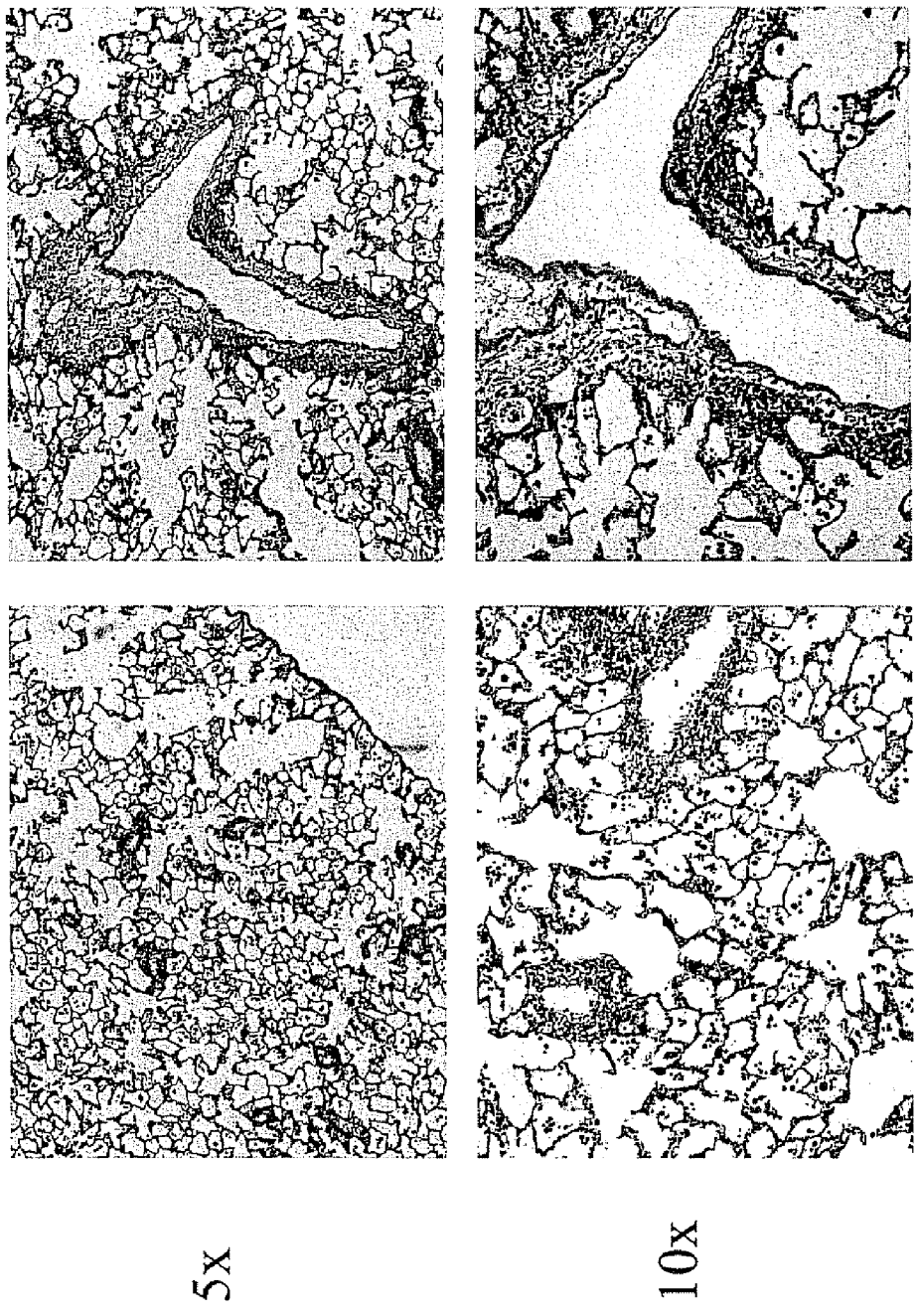
Fig 16 Juglone allogenic tx day 8 after transplantation

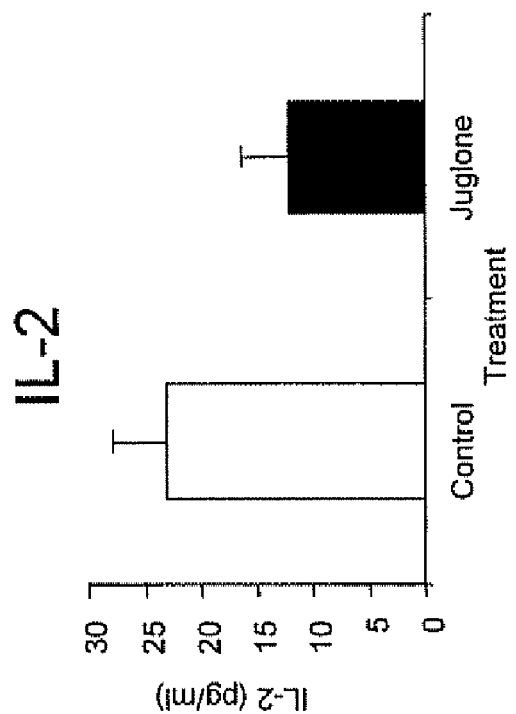
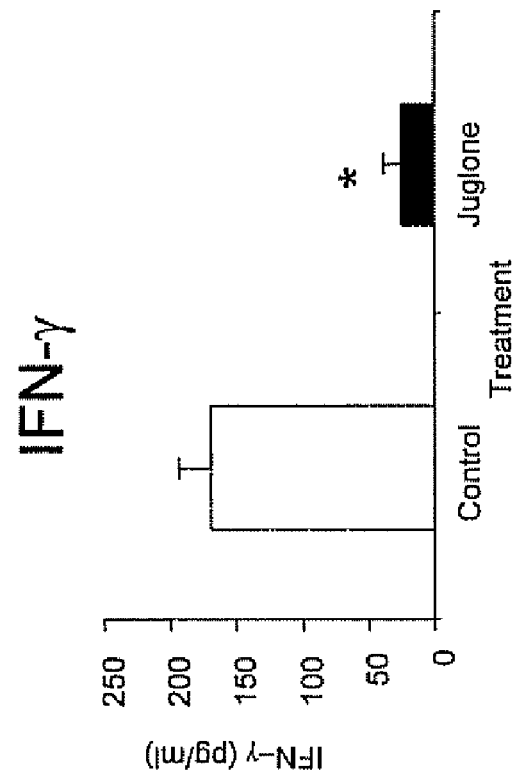
Fig. 21

US 7,417,072 B2

BLOCKADE OF PIN1 PREVENTS CYTOKINE PRODUCTION BY ACTIVATED IMMUNE CELLS

This application claims priority to U.S. provisional patent applications, Ser. Nos. 60/680,387 and 60/680,441, both filed May 12, 2005, the disclosures of each of which are explicitly incorporated by reference herein.

These studies were funded by a grant from the National Institute of Health, grant number HL056396. The U.S. government has certain rights in this invention

FIELD OF THE INVENTION

The invention relates to pharmaceutical compositions and methods for treating immunological disorders. In particular, the invention relates to pharmaceutical compositions and methods for treating eosinophil-associated disorders and methods for inducing eosinophil apoptosis in an individual in need thereof. The invention also provides pharmaceutical compositions and methods for blocking cytokine expression by activated immune and other cells, and methods and pharmaceutical compositions for preventing or reducing organ transplant rejection

BACKGROUND OF THE INVENTION

The mammalian hematopoietic system comprises a number of cell types that mediate cellular immunity. While being vital to good health in a mammalian organism, dysregulation of the complex immunological systems has been implicated to play a role in a number of pathological diseases and disorders. In addition, there are instances, such as in organ transplantation, where even normal operation of the immunological system can be disadvantageous and have unwanted consequences.

One example of a disease state in a mammal in which the immunological system is thought to play a role is asthma. A population of eosinophils isolated from peripheral blood from normal individuals contains about 5% surviving cells after 3 days of culture. In contrast, cultures of eosinophils isolated from asthmatic individuals contain about 95% surviving cells after 3 days. That this difference is important in the etiology of asthma in humans is supported by work in human and mouse asthma models, where asthma can be induced by injecting the animal with allergen followed by inhalation challenge with that allergen. Significantly, asthma does not result when this protocol is used in mice that lack eosinophils. A role in asthma for eosinophils is further indicated by certain physiologic properties of eosinophils; for example, these cells can release vasoactive materials and cytokines and can lead to scarring of lung tissues. The effects of asthma may be reduced or eliminated by eliminating or reducing eosinophil populations in lungs in asthma patients.

Thus, there is a need in the art for clinically effective compounds and pharmaceutical agents that can inhibit or reduce eosinophil survival or persistence in the lungs of patients who have disorders, such as asthma, that are associated with increased eosinophil activation and accumulation. Similarly, there is a need in the art for more effective methods for treating tissue and organ transplant recipients, to reduce the vigor and persistence of a transplant recipient's immunologic rejection of donor tissues and organs.

SUMMARY OF THE INVENTION

The invention provides pharmaceutical compositions and methods for treating or preventing immunological disorders, including pathological diseases and disorders caused by dysregulation of the immunological system or cells comprising the immunological system in an animal, and disorders such as occur in organ transplantation recipients where normal functioning of the immunological system or cells comprising the immunological system result in a pathology such as transplant rejection. As provided herein, the invention provides pharmaceutical compositions comprising a Pin1 inhibitor compound, and methods for using said pharmaceutical compositions comprising the step of administering therapeutically effective amounts of a Pin1 inhibitor, and/or pharmaceutically acceptable salts thereof, to a patient in need of such treatment.

In certain aspects, the invention provides pharmaceutical compositions and methods for treating diseases and disorders characterized or associated with pathological activity or dysregulation of the immunological system or cells comprising the immunological system. In particular aspects, the invention provides pharmaceutical compositions and methods for inducing apoptosis in immune cells, such as peripheral blood mononuclear cells and particularly eosinophils, comprising the step of contacting said cells with a Pin1 inhibitor or pharmaceutical composition thereof.

In other aspects, the invention provides pharmaceutical compositions and methods for inhibiting or reducing the pathological effects induced by the presence, and particularly the overabundance, persistence, or activation of immune cells, such as peripheral blood mononuclear cells and particularly eosinophils, the method comprising the step of administering a therapeutically effective amount of a Pin1 inhibitor, and/or pharmaceutically acceptable salts thereof, to a patient that has or is suspected of having an immunological disease or disorder, particularly such a disease or disorder characterized by the overabundance, persistence or activation of eosinophils. In particular embodiments, the method involves inducing apoptosis in the peripheral blood mononuclear cells and particularly eosinophils. In particular embodiments, the invention provides pharmaceutical compositions and methods for treating asthma.

In other aspects, the invention further provides pharmaceutical compositions and methods for ameliorating acute and chronic tissue rejection caused by tissue transplantation, including organ transplantation, comprising the step of administering therapeutically effective amounts of one or more Pin1 inhibitors to a patient in need thereof. In a particular aspect, an organ transplant recipient can be treated with a Pin1 inhibitor prior to surgery, during surgery, and/or after surgery.

Specific preferred embodiments of the invention will become evident from the following more detailed description of certain preferred embodiments and the claims

BRIEF DESCRIPTION OF THE DRAWINGS

FIGS. 1A-1C show that Pin1 was required for eosinophil (Eos) survival. In FIGS. 1A and 1B, purified Eos were untreated (R), treated with hyaluronic acid (HA) alone (HA, 100 μg/ml, used in all experiments), HA plus cyclosporine (CsA) (HA+CsA), recombinant human GM-CSF (rhGM-CSF) (GM, 100 pg/ml) alone, rhGM-CSF plus CsA, HA plus juglone (HA+Jug) or rhGM-CSF plus juglone for 4 days at the concentrations shown prior to viability assay. In FIG. 1C, cells were untreated (−), or treated with HA or HA plus juglone for 4 h or 24 h. Immunoblot analysis of cell lysates was performed using anti-caspase 3 antibody. β-actin served as an internal loading control.

FIGS. 2A-2E show that Pin1 inhibition accelerated GM-CSF mRNA decay in eosinophils. In FIG. 2A, Eos were treated as in FIG. 1A for 4 h prior to lysis with TriReagent and RT-PCR/Southern blot analysis for GM-CSF mRNA. Gel electrophoresis of GM-CSF products and control β-actin RT-PCR products are shown. In FIG. 2B, cells were treated with HA for 4 h and then juglone (1 μM) was added at the indicated times before harvest and RT-PCR analysis, where GM-CSF or β-actin mRNA expression were analyzed as above. In FIG. 2B, "C," refers to PCR reaction mixtures without added cDNA. In FIG. 2C, cells were untreated (−/− lanes on left) or incubated for 4 h with HA atone, HA plus varying concentrations (160 or 320 nM) of TAT-conjugated green fluorescent protein (TAT-GFP) or TAT-conjugated Pin1 domains (TAT-wwPin1) and analyzed as in FIG. 2A. In FIG. 2D, control (−/−), HA (100 μg/ml), rhGM-CSF (100 pg/ml), HA or GM-CSF plus TAT-GFP (160 nM) or HA or GM-CSF plus TAT-wwPin1 (160 nM) treated Eos were cultured for 4 days prior to cell viability assay as disclosed in Example 2 below. In FIG. 2E, eosinophils were treated for 4 h with HA or HA plus juglone (1 μM, 1 h prior to harvest) prior to the addition of actinomycin D (5 μg/ml) and cells harvested at the indicated times for RT-PCR/Southern blot analysis. In these experiments, PCR was performed for 30 (HA-treated cells) or 33 (HA plus juglone-treated cells) cycles, respectively. The calculated half-life of GM-CSF mRNA is shown below the panel.

FIGS. 3A-3D show that Pin1 associated with AUF1 (AU-rich element RNA-binding protein 1). In FIG. 3A, Eos were untreated (−/−), treated with HA or HA plus juglone (1 μM) for 4 h. Cell lysates were immunoprecipitated with anti-Pin1 antibody followed by immunoblotting with anti-AUF1 or anti-Pin1 antibodies. Nonimmune IgG was used as a negative control while HeLa cell extracts were used as a positive control ("C"). In FIG. 3B, immunoblots of cytoplasmic protein from Eos treated for 4 h with HA and co-treated with juglone (1 μM) for the indicated times before harvest. In FIG. 3C, cells were untreated (−/−/−) treated for 4 h with HA alone, HA plus juglone (10 min before harvest) or HA plus 20 μM or 100 μM MG132 (4 h) plus juglone (10 min before harvest), Cell lysates were immunoblotted with the antibodies shown. Lane "C" is a HeLa cell lysate used as a positive control. In FIG. 3D, Eos were treated as described for FIG. 3C except that only 20 μM MG132 was used. Cells were lysed with TriReagent for total RNA isolation prior to RT-PCR/Southern blot analysis.

In FIG. 4A, cells were untreated (R), treated with HA for 4 h or HA plus juglone (1 μM, added 10 min before harvest) (HA+J10') and lysed. Forty percent of the lysate was used for total RNA isolation and the remaining 60% for AUF1 immunoprecipitation. Both samples were then analyzed for β-actin and GM-CSF mRNA by RT-PCR/Southern blot analysis. In FIG. 4B, cells were untreated (−/−), treated with HA for 4 h or HA plus TAT-wwPin1 (as described below in Example 4; 100 nM) (incubated for the indicated times before harvest) prior to lysis and immunoprecipitation (IP) with the indicated antibodies. 40% of the lysate was used for RT-PCR/Southern blot and remaining 60% was western blotted with anti-His to detect AUF1 associated TAT-wwPin1. Lane "C" in FIG. 4A refers to PCR without added cDNA; Lane "C" in FIG. 4I is a positive GM-CSF PCR control.

FIG. 6 shows hypothetical Pin1 sites (S/T-Pro) in human AREBPs as identified by screening of the NCBI protein database. Co-immunoprecipitation (IP) results are shown by "+".

FIG. 14A-D shows that cytokine mRNAs and DNA synthesis are suppressed by Pin1 inhibition in activated splenocytes. In FIG. 14A, mRNAs for IFN-γ, IL-2, TNF-α, CXCL-10 and TGF-β were analyzed in rat splenocytes by reverse transcription, qPCR. The ionomycin/PMA stimulated sample was normalized to 100 and others expressed as a % of that value. The data are averages±SEM of 3 independent experiments using splenocytes of untreated healthy animals. FIG. 14B shows graphs of secreted IFN-γ and IL-2 after 24 hours from the cultures as described in FIG. 14A, FIG. 14C shows representative cell viability after 24 hours of the cultures treated as described in FIG. 14A. Cells were stained with propidium iodide and analyzed by flow cytometry. The results shown are representative of 3 experiments. FIG. 14D shows a graph representing BrdU incorporation after 48 hours of culture under conditions as described in FIG. 14A; open columns, no exogenous IL-2; shaded columns, IL-2 (2 ng/ml) added 24 hour after the initiation of culture. The data are averages±SEM of 3 independent experiments using splenocytes of untreated healthy animals.

FIG. 15 shows that WKY rats rejected orthotopic lung transplants from F344 rats, WKY rats (weight 250-300 g) each had their left lung removed and replaced with an allogenic lung from F344 donor rats. The bronchus and pulmonary vessels were reconnected, chests sutured and the animals returned to their cages. Daily, 10 ml of normal saline was injected IP to maintain hydration. After 8 days, the animal was sacrificed and both lungs removed, bronchoalveolar lavage (BAL) performed and lungs gently inflated with 4% formaldehyde for 2 days. After dehydration and paraffin embedding, random sections were prepared and stained using standard methods with H & E (hemotoxylin and eosin) and examined for pathology. Representative 5× and 10× microscopic views are shown. Hemorrhagic necrosis, massive inflammation and total effacement of alveoli was seen. Spleens from untreated animals were also harvested for Elispot and RT-qPCR.

FIG. 16 shows that WKY rats did not reject allogeneic lung transplants if treated daily with 1 mg/kg juglone. Animals were treated as in FIG. 15 above except that on the day of surgery and each subsequent day, they received via IP injection 1 mg/kg juglone dissolved in 10 ml of saline. These photomicrographs of representative lung tissue were prepared using the same magnification as shown as for control animals in FIG. 15 above. This Figure shows that lung architecture and alveolar spaces were maintained in the juglone-treated transplanted animals, and that there was a lack of immune cell infiltration or damage in the transplanted lungs in rats treated with juglone.

FIG. 19A and FIG. 19D show the gross appearance of lungs from control, untreated transplants (FIG. 19A) and juglone treated (1 mg/kg; FIG. 19D). Lungs are oriented so that transplant is on the left, FIG. 19B and FIG. 19E show hematoxylin and eosin stained sections from control untreated (FIG. 19B) or juglone treated (FIG. 19E). FIG. 19C and FIG. 19F, show trichrome stained sections of control, untreated (FIG. 19C) and juglone treated (FIG. 19F). These are representative sections from 8 control and 8 juglone treated transplant recipients.

FIG. 20 shows Pin1 activity is blocked in the BAL cells from juglone treated animals.

FIG. 21 shows that blocking Pin1 inhibits IFN-γ production in vivo, IFN-γ and IL2 concentrations in BAL fluid were determined by ELISA. Data are shown as the average±SEM (n=4 rats) of 3 experiments 7 days after transplantation. Lavage fluid was concentrated 10 fold prior to analysis. Lavage recovery was similar in all animals and the data shown are those from the concentrated samples. * denotes p<0.01.

FIG. 22 shows IFN-γ, CXCL10 and ColI are most affected by PinI blockade.

FIG. 24A shows lungs from an animal treated with CsA at 1 mg/kg/d for 3 days. FIG. 24B shows lungs from an animal treated with juglone at 0.1 mg/kg/d for 7 days. FIG. 24C shows lungs from an animal treated with CsA at 1 mg/kg/d for 3 days plus juglone at 0.1 mg/kg/d for 7 days. For all conditions, gross appearance of the transplant at harvest shown along the left, 5× and 20× representative sections stained with H & E shown in the middle and right panels.

DETAILED DESCRIPTION OF THE PREFERRED EMBODIMENTS

Figure 4:
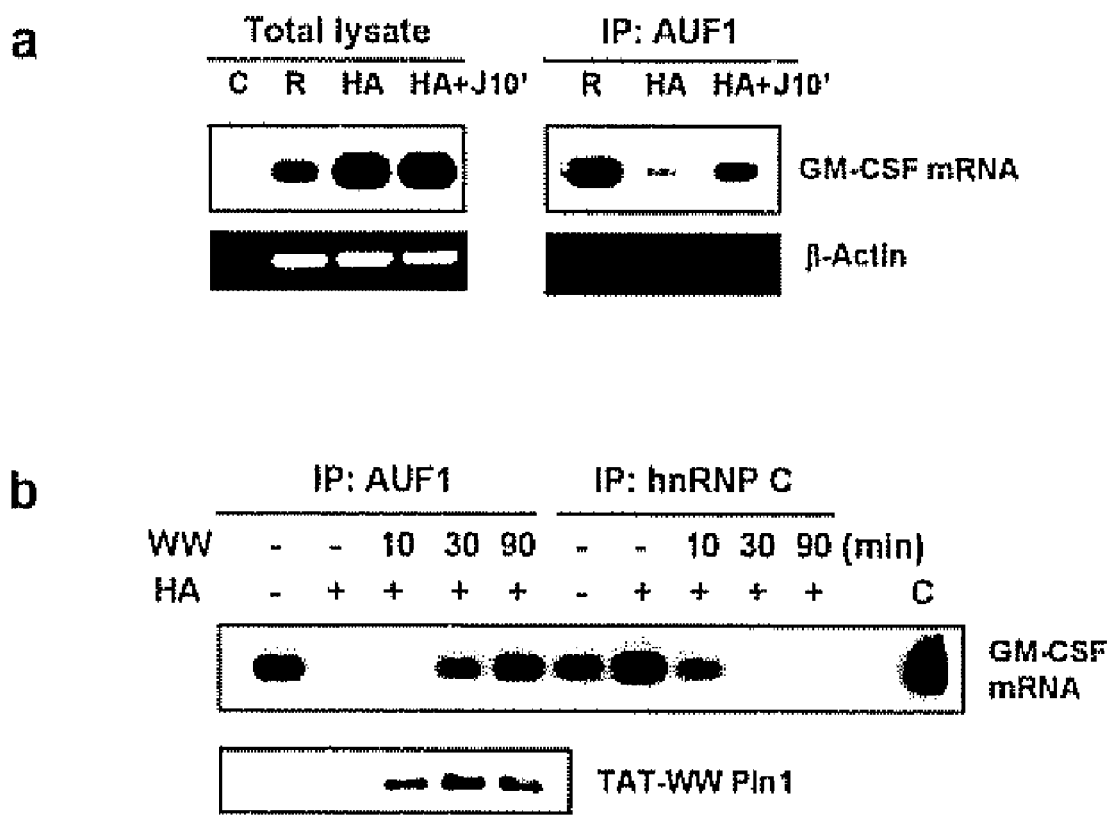
FIGS. 4A-4B show that GM-CSF mRNA partitioned between different AU-rich mRNA binding proteins (AREBPs).

This invention provides compositions and methods for reducing levels, amounts or activities of immune cells, particularly by inducing apoptosis in immune cells. The compositions and methods of this invention are directed specifically to peripheral blood mononuclear cells and particularly eosinophils. As disclosed herein, the compositions and methods of the invention comprise the step of contacting said cells with a Pin1 inhibitor or pharmaceutical composition thereof.

In certain embodiments, the invention provides pharmaceutical compositions and methods of treating or preventing an immunological disorder in a patient who has or is suspected of having an immunological disorder, the method comprising administering to said patient one or a plurality of Pin1 inhibitors. Immunological disorders includes generally pathological diseases and disorders caused by dysregulation of the immunological system or cells comprising the immunological system in an animal, and disorders such as occur in organ transplantation recipients where normal functioning of the immunological system or cells comprising the immunological system result in a pathological result such as transplant rejection. The invention particularly provides pharmaceutical compositions comprising a Pin1 inhibitor compound, and methods for using said pharmaceutical compositions by administering a therapeutically-effective amount of the pharmaceutical composition of a Pin1 inhibitor, and/or pharmaceutically acceptable salts thereof, to a patient in need of such treatment.

As used herein, the terms "patient," "mammal" and "animal" includes human and animal subjects.

As used herein, "treatment" or "treat" refers to both therapeutic treatment and prophylactic or preventative measures. Those in need of treatment include those already having an immunological disorder as well as those prone to have the disorder or those in which the disorder is to be prevented.

As used herein, a "disorder" is any condition that would benefit from treatment according to the present invention "Disorder" and "condition" are used interchangeably herein and include chronic and acute immunological disorders or immunological diseases associated with inappropriate immune response, including those pathological conditions which predispose a mammal to an immunological disorder.

As used herein, an "immunological disorder" encompasses any medical condition or disorder in which immune cells infiltrate a tissue and/or organ thereby causing damage or loss of function including, but not limited to, eosinophil-associated disorders, autoimmune disease, graft survival, bone marrow and organ transplantation, allosensitization due to blood transfusions, toxic shock syndrome, T-cell dependent B-cell mediated diseases, chronic inflammatory diseases associated with chronic immune cell dysfunction, lymphoproliferative disorders (such as multiple myeloma, Waldenstom's macroglobulinemia, and cryoglobulinemias), and cancer. Non-limiting examples of autoimmune diseases include systemic lupus erythematosis, rheumatoid arthritis, immune thrombocytopenic purpura (ITP), multiple sclerosis, diabetes, and psoriasis. Non-limiting examples of chronic inflammatory diseases include inflammatory bowel disease (such as Crohn's disease and ulcerative colitis), Grave's disease, Hashimoto's thyroiditis, and diabetes mellitus.

The terms "immunological disease" and "immunological disorder" also encompass any clinical condition that would be ameliorated by the inhibition of antibody production, such as hypersensitivity reactions. Hypersensitivity reactions can be caused, for example, by hay fever, allergies, asthma, atopy, and acute edema. Non-limiting examples of diseases that cause antibody-mediated hypersensitivity reactions include systemic lupus erythematosis, arthritis (such as rheumatoid arthritis, reactive arthritis, psoriatic arthritis), nephropathies (such as glomerulo-nephritis, membranous, mesangiocapillary, focal segmental, focal necrotizing, crescentic, proliferative-tubulopathies), skin disorders (such as pemphigus and pemphigoid, erythema nodosum), endocrinopathies (such as thyroiditis, Grave's disease, Hashimoto's disease, and insulin dependent diabetes mellitus), various pneumopathies (such as extrinsic alveolitis), various vasculopathies, coeliac disease, diseases with aberrant production of IgA, many anemias and thrombocytopenias, Guillain-Barre Syndrome, and myasthenia gravis.

In other embodiments, the invention provides pharmaceutical compositions and methods directed towards specific cellular components of an animal's immune system, particularly eosinophils. In particular embodiments, the invention provides pharmaceutical compositions and methods for reducing levels, amounts or activities of immune cells, particularly by inducing apoptosis in immune cells. The inventive compositions and methods are specifically directed towards peripheral blood mononuclear cells, especially eosinophils. In yet other embodiments, the invention provides methods of treating a patient who has or is suspected of having an immunological disorder, such as a disorder characterized by or associated with a peripheral blood mononuclear cell particularly eosinophils, the method comprising inducing apoptosis in said cells, and in particular eosinophils in said patient.

As used herein, a disorder "characterized or associated with a peripheral blood mononuclear cell" and an "eosinophil-associated disorder" refers to a biological condition or pathology in which the levels of activation and accumulation of peripheral blood mononuclear cells, particularly eosinophils, are elevated and play a significant role in the pathophysiology of the condition. Non-limiting examples of eosinophil-associated disorders include hypersensitivity diseases such as bronchial asthma, chronic eosinophilic pneumonia, vernal conjunctivitis, allergic conjunctivitis, allergic rhinitis, allergic sinusitis, and allergic gastroenteropathy, and other eosinophil-associated diseases such as eosinophilic gastroenteritis, atopic dermatitis, bullous pemphigoid, eosinophilia-associated episodic angioedema, and ulcerative colitis.

In a particular embodiments, the invention provides methods and pharmaceutical compositions for inducing apoptosis in peripheral blood mononuclear cells, particularly eosinophils. As provided herein, apoptosis of peripheral blood mononuclear cells, particularly eosinophils is induced by contacting said cells with one or a plurality of Pin1 inhibitors. As used herein, a "Pin1 inhibitor" can be, for example, a dominant negative peptide, an antibody, antisense oligonucleotide, or a short interfering nucleic acid molecule (siRNA), or a small molecule inhibitor, for example, juglone or PiB (diethyl-1,3,6,8-tetrahydro-1,3,6,8phorylated tetraoxobenzo[lmn] phenanthroline-2,7-diacetate ethyl 1,3,6,8-tetrahydro-1,3,6,8-tetraoxo-benzo[lmn] phenanthroline-(2H, 7H)-diacetate).

A "dominant negative peptide" is a variant of a protein that can displace an active protein from its interaction with the cellular machinery or that can compete with the active protein, thereby reducing the effect of the active protein. For example, expression or introduction of a dominant negative Pin1 peptide in a peripheral blood mononuclear cell, particularly an eosinophil cell will cause a reduction in function of active Pin1 protein and induce apoptosis, such as the TAT-WWPin1 dominant negative inhibitor as described in the Examples below. One of ordinary skill in the art can assess the potential for a dominant negative variant of a Pin1 protein, and using standard mutagenesis techniques can create one or more dominant negative variant polypeptides effective in the methods of the invention. For example, the sequence of native Pin1 peptides can be mutated by site-specific mutagenesis, scanning mutagenesis, partial gene deletion or truncation, and the like (for example see Sambrook et al, 2001, *Molecular Cloning: A Laboratory Manual*, 3rd ed., Cold Spring Harbor Laboratory Press, Cold Spring Harbor, N.Y.). The population of mutagenized Pin1 peptides can be tested for reduction or inhibition of Pin1 activity using, for example, the methods described in the Examples below. Said peptides can be introduced into cells directly, either alone or conjugated to a targeting or carrier molecule, for example, via a penetratin tag (HIV or antennaepedia), or can be expressed in said cells by targeted introduction of genetic constructs encoding the peptides (e.g. encoded by a polynucleotide introduced into a cell in a viral vector).

In other embodiments, the invention provides antibodies or immunologically functional fragments thereof that selectively bind to Pin1 and methods for selectively inhibiting or interfering with the activity of Pin1 proteins. Standard methods for preparation of monoclonal and polyclonal antibodies and immunologically active fragments thereof are well known in the art, for example as described in Harlow and Lane (1988, ANTIBODIES: A LABORATORY MANUAL, Cold Spring Harbor Laboratory Press: New York). Methods for generating antibody fragments, particularly Fab fragments and other fragments that retain epitope-binding ability and specificity are also well known, as are fully human antibodies and chimeric antibodies, including "humanized" antibodies. "Humanized" antibodies include, for example, antibodies generated in mice that are "humanized" to reduce negative immune effects that can occur during administration to human subjects by replacing certain portions of the mouse antibody with portions of human antibodies. Thus, the invention encompasses use of antibody inhibitors of Pin1 that include, but are not limited to, single chain antibodies, single chain Fv antibodies, F(ab) antibodies, F(ab)' antibodies and (Fab')$_2$ antibodies, chimeric antibodies in which one or more regions have been replaced by homologous human or non-human portions, and fully human antibodies. Single chain antibodies are discussed in detail in International Patent Application Publication No. WO 88/01649 and U.S. Pat. Nos. 4,946,778 and 5,260,203. Such inhibitors can be delivered, for example, via a penetratin tag (HIV or antennaepedia) or by recombinant means (e.g. encoded by a polynucleotide introduced into a cell in a viral vector).

In additional embodiments, antisense oligonucleotides can be used to inhibit Pin1 activity to induce apoptosis in peripheral blood mononuclear cells, particularly eosinophils. Such antisense oligonucleotides can be nucleic acid molecules that are complementary to and hybridize to expression control sequences (triple helix formation) or to Pin1 mRNA. For example, antisense DNA or RNA molecules, which have a sequence that is complementary to at least a portion of a Pin1 gene can be introduced into a cell. Antisense probes may be designed by available techniques using the sequence of the Pin1 gene as known in the art. Typically, each such antisense molecule will be complementary to the start site (5' end) of the Pin1 in RNA. When the antisense molecule hybridizes to the corresponding Pin1 mRNA, translation of this mRNA is prevented or reduced.

In other embodiments, a Pin1 inhibitor can be a short interfering RNA (siRNA). The term "short interfering RNA" or "siRNA" as used herein refers to a double stranded nucleic acid molecule capable of RNA interference or "RNAi", as disclosed, for example, in Bass, 2001, *Nature* 411: 428-429; Elbashir et alt, 2001, *Nature* 411: 494-498; and Kreutzer at al., International PCT Publication No, WO 00/44895; Zernicka-Goetz et al., International PCT Publication No. WO 01/36646; Fire, International PCT Publication No. WO 99/32619; Plaetinck et al., International PCT Publication No, WO 00/01846; Mello and Fire, International PCT Publication No. WO 01/29058; Deschamps-Depaillette, International PCT Publication No. WO 99/07409; and Li et al., International PCT Publication No. WO 00/44914. As used herein, siRNA molecules need not be limited to those molecules containing only RNA, but may further encompass chemically modified nucleotides and non-nucleotides having RNAi capacity or activity. siRNA molecules can be designed using methods known in the art, for example, using algorithms and products available through Ambion, Inc. (Austin, Tex.).

A Pin1 siRNA molecule of the invention can be a double-stranded polynucleotide molecule comprising self-complementary sense and antisense regions, wherein the antisense region comprises a nucleotide sequence that is complementary to the nucleotide sequence of Pin1 or a portion thereof and the sense region has a nucleotide sequence corresponding to the Pin1 nucleic acid sequence or a portion thereof. The Pin1 siRNA molecule can be assembled from two separate oligonucleotides, where one strand is the sense strand and the other is the antisense strand, wherein the antisense and sense strands are self-complementary. The Pin1 siRNA molecule can also be assembled from a single oligonucleotide having self-complementary sense and antisense regions linked by means of a nucleic acid based or non-nucleic acid-based linker. The Pin1 siRNA molecule can be a polynucleotide that can form a substantially symmetrical duplex, asymmetric duplex, hairpin, or asymmetric hairpin secondary structure. The Pin1 siRNA molecule can also comprise a single stranded polynucleotide having nucleotide sequence complementary to the Pin1 nucleotide sequence or a portion thereof, wherein the single stranded polynucleotide can further comprise a terminal phosphate group, such as a 5',3'-diphosphate or a 5'-phosphate as discussed, for example, in Martinez et al., 2002, *Cell* 110:563-574 and Schwarz et al, 2002, *Molecular Cell* 10:537-568.

A Pin1 siRNA molecule of the invention comprising a single stranded hairpin structure can be about 36 to about 70 nucleotides in length, having two complementary sequences of about 15 to about 30 nucleotides separated by a spacer sequence that allows hybridization of the complementary sequences. Thus, the single stranded hairpin structure has about 15 to about 30 base pairs comprising the duplex portion of the molecule. In one embodiment, the hairpin siRNA has about 18, 19, 20, or 21 base pairs in the duplex portion and a loop portion of a length that accommodates hybridization of the complementary siRNA sequences. Human Pin1 is encoded by a nucleic acid sequence identified by Accession No. NM_006221 (GenBank, NCBI) from which efficacious siRNA species can be identified.

In yet other embodiments, Pin1 activity can be inhibited using small molecule inhibitors. Libraries of small organic molecules can be obtained commercially (for example, ChemBridge Corp., San Diego, Calif., and LION Biosciences, Cambridge, Mass.) or can be prepared according to standard methods (for example, Thompson and Ellman, 1996, *Chem. Rev.* 96:555-600). The small molecule libraries can be screened or assayed for inhibitors of Pin1 using, for example, the methods described in the Examples below. In a particular embodiment, juglone, pharmaceutically acceptable salts of juglone, and/or compositions comprising juglone are useful as small molecule inhibitors of Pin1.

In certain embodiments, small molecule Pin1 inhibitors can be developed using structure-based drug design based on the structural characteristics of known Pin1 inhibitors, such as juglone. Various methods of structure-based drug design are disclosed in the art, for example, in Maulik et al., 1997, Molecular Biotechnology: Therapeutic Applications and Strategies, Wiley-Liss, Inc., which, like all references, applications, and patents disclosed herein, is incorporated herein by reference in its entirety Maulik et al disclose, for example, methods of directed design, in which a user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate inhibitors/compounds/apoptosis inducers; and a grid-based approach in which the user calculates the interaction energy between three dimensional receptor structures and small fragment probes, followed by linking together of favorable probe sites.

Several computer programs are known in the art that can be used in designing a potential inhibitor of the invention, including, but not limited to:

GRID (Goodford, 1985, *J Med. Chem.* 28:849-857, which is a program that determines probable interaction sites between probes with various functional group characteristics and the macromolecular surface, can be used to analyze the surface sites to determine structures of similar inhibiting proteins or molecules. The GRID calculations, with suitable inhibiting groups on molecules (e.g., protonated primary amines) as the probe, are used to identify potential hotspots around accessible positions at suitable energy contour levels. GRID is available from Oxford University, Oxford, UK;

MCSS (Miranker and Karplus, 1991, *Proteins: Structure, Function and Genetics* 11:29-34). MCSS is available from Molecular Simulations, Burlington, Mass., AUTODOCK (Goodsell and Olsen, 1990, *Proteins, Structure, Function, and Genetics* 8:195-202). AUTODOCK is available from Scripps Research Institute, La Jolla, Calif.;

DOCK (Kuntz et al., 1982, *J. Mol. Biol.* 161: 269-288). The program DOCK may be used to analyze an active site or ligand binding site and suggest ligands with complementary steric properties. DOCK is available from University of California, San Francisco, Calif.;

ALADDIN (Van Drie et al, 1989, *J. Comp-Aided Mol. Des* 3:225);

CLIX (Davie and Lawrence, 1992, *Proteins* 12:31-41);

GROUPBUILD (Rotstein and Murcko, 1993, *J. Med. Chem.* 36:1700),

GROW (Moon and Howe, 1991, *Proteins* 11:314);

LUDI (Bohm, 1992, *J. Comp. Aid. Molec. Design* 6:61-78; and Rotstein and Murcko, 1992, *J. Med. Chem.* 36:1700-1710). LUDI is available from Biosym Technologies, San Diego, Calif.;

LEGEND (Nishibata and Itai, 1991, *Tetrahedron* 47:8985). LEGEND is available from Molecular Simulations, Burlington, Mass.; and LeapFrog (available from Tripos Associates, St. Louis, Mo.).

Other molecular modeling techniques can also be used in accordance with the invention, including, but not limited to, Cohen et al, 1990, *J. Med Chem* 33:883-894; Navia and Murcko, 1992, *Current Opinions in Structural Biology* 2:202-210; and Jorgensen, 1998, "BOSS-Biochemical and Organic Simulation System" in the Encyclopedia of Computational Chemistry (P. V. R. Schleyer, ed.) Wiley & Sonstra., Athens, U.S.A. 5:3281-3285).

In one embodiment, it can be possible during modeling to introduce into a potential inhibitor chemical moieties that may be beneficial for a molecule that will be administered as a pharmaceutical. For example, it may be possible to introduce into or omit from the potential inhibitor, chemical moieties that may not directly affect binding of the inhibitor to Pin1 but that contribute, for example, to the overall solubility of the inhibitor in a pharmaceutically acceptable carrier, the bioavailability of the inhibitor and/or the toxicity of the inhibitor. Considerations and methods for optimizing the pharmacology of the inhibitors of interest can be found, for example, in "Goodman and Gilman's The Pharmacological Basis of Therapeutics," 1985, Eighth Edition (Goodman Gilman, Rall, Nies, & Taylor, eds.), Pergaman Press; Jorgensen and Duffy, 2000, *Bioorg. Med. Chem. Lett.* 10:1155-1158.

Also, the computer program "QikProp" (Schrodinger, Portland, Oreg.) can be used to provide rapid predictions for physically significant descriptions and pharmaceutically-relevant properties of an organic molecule of interest.

Potential inhibitors can also be selected based on their structural similarity to Pin1 inhibitors, such as juglone, by systematically modifying a structural analog with computer modeling programs. For example, such analysis has been described for developing HIV protease inhibitors (Lam et al, 1994, *Science* 263:380-384; Wlodawer et al., 1993, *Ann. Rev. Biochem.* 62:543-585; Appelt, 1993, *Perspectives in Drug Discovery and Design* 1:23-48; Erickson, 1993, *Perspectives in Drug Discovery and Design* 1:109-128).

A candidate inhibitor designed using computer modeling can be obtained from a commercial library of chemicals or synthesized de novo. Appropriate methods of chemical synthesis include medicinal chemistry and combinatorial chemistry techniques known to those of skill in the art (see, for example, Advanced Organic Chemistry $2^{nd}$ edition (J. March) 1977, McGraw-Hill New York and B. A. Bunin, The Combinatorial Index, 1998, Academic Press).

A candidate inhibitor can be screened for binding activity in one of many conventional binding assays, such as, for example, a radioligand receptor binding assay on a solid support, or a fluorescence-polarization assay conducted in solution (See for example, Immune and Receptor Assays in Theory and in Practice, Patrick Englebienne, CRC Press 2000).

Determining whether a potential inhibitor inhibits the activity of Pin1 can be accomplished using, for example, an eosinophil apoptosis assay as described in the Examples below.

In another embodiment, methods of the invention for identifying Pin1 inhibitors comprises the steps of: (a) screening one or a plurality of organic compounds that are structurally related to a Pin1 inhibitor, such as juglone; and (b) determining whether the potential inhibitor inhibits the activity of Pin1. In one aspect, the screening comprises using a pharmacophore or structural feature identified by analysis of structure/activity relationship, inter alia, using computer-assisted modeling tools as described above. Determining the activity of a potential inhibitor can be accomplished as described above.

In another embodiment, the invention provides methods of identifying a compound for treating an immunological disorder, comprising: (a) providing a plurality of cells that express Pin1, (b) assaying the cells in the presence and absence of a candidate compound for activity of Pin1; and (c) identifying the compound as a compound for treating an immunological disorder if the Pin1 activity is less in the presence of the candidate compound than in the absence of the candidate compound. Assaying for Pin1 activity can be accomplished, for example, using methods described herein.

The concept of the pharmacophore has been well described in the literature (see, for example, Mayer et al, 1987, *J. Comp. Aided Molec. Design* 1:3-16; Hopfinger and Burke, 1990, Concepts and Applications of Molecular Similarity, M. A. Johnson and G. M. Maggiora, ed., Wiley). In one embodiment, a pharmacophore of the invention is generated based on the most important common structural features of a Pin1 inhibitor, such as juglone. As used herein, "pharmacophore computer programs" encompass software used for computational mining of three-dimensional (3-D) molecular databases to identify compounds that are structurally similar to Pin1 inhibitors, such as juglone, and can inhibit Pin1 activity.

Pharmacophore computer programs that can be used in a method of the invention include, but are limited to: DISCO (Abbot Laboratories, Abbot Park, Ill.); Catalyst (Bio-CAD Corp., Mountain View, Calif.); and Chem DBS-3D (Chemical Design Ltd., Oxford, U.K.).

Databases of chemical structures are available from, for example, Cambridge Crystallographic Data Center (Cambridge, U.K.) and Chemical Abstracts Service (Columbus, Ohio).

Once a potential inhibitor is identified using a method of the invention, the potential inhibitor can be examined through the use of computer modeling using a docking program such as GRAM, DOCK or AUTODOCK (Dunbrack et al., 1997, *Folding & Design* 2:R27-42). This procedure can include, for example computer fitting of candidate compounds to the Pin1:juglone binding site to ascertain how well the shape and the chemical structure of the potential inhibitor will complement the binding site. (Bugg et al, 1993, *Scientific American* December:92-98; West et al., 1995, *TIPS* 16:67-74). Computer programs can also be used to estimate the attraction, repulsion and steric hindrance of the two binding partners (i.e. the ligand-binding site and the candidate compound).

In another embodiment of the invention, structural analogs of Pin1 inhibitors, such as juglone, that successfully inhibit Pin1 can be, systematically modified by computer modeling programs to enhance binding properties. For example, such compounds can be modified to satisfy criteria associated with chemical complementarity, such as hydrogen bonding, ionic interactions or Van der Waals interactions.

Once a candidate compound is identified it can be either selected from a library of chemicals as are commercially available or, alternatively, the candidate compound can be synthesized de novo. De novo synthesis of one or even a relatively small group of specific compounds is known in the art of drug design.

A candidate compound can be placed into a standard binding assay with Pin1 or a fragment of Pin1 that comprises the Pin1 inhibitor binding site to determine if the compound can bind Pin1. A candidate compound can also be used in a Pin1 activity assay as described herein to determine if the compound can inhibit Pin1 activity.

One of ordinary skill in the art can readily use the assays described herein and those well known in the art to determine whether a dominant negative Pin1 peptide, a Pin1 antibody, variant, fragment, siRNA molecule, or small molecule Pin1 inhibitor is a functional inhibitor of Pin1 using no more than routine experimentation. For example, the activity can be tested for the ability to induce apoptosis in eosinophils as described in the Examples below.

In preferred embodiments, methods of the invention comprise the step of administering a pharmaceutical composition comprising a therapeutically effective amount of one or a plurality of Pin1 inhibitors together with a pharmaceutically acceptable diluent, carrier, solubilizer, emulsifier, preservative and/or adjuvant, wherein the pharmaceutical composition is capable of inducing a desired therapeutic effect when properly administered to a patient. Preferably, acceptable formulation materials are nontoxic to recipients at the dosages and concentrations employed.

The expression "therapeutically effective" in reference to a pharmaceutical composition comprising one or a plurality of Pin1 inhibitors is understood to mean, according to the invention, an amount of the said pharmaceutical composition that is capable of preventing or reducing the pathological effects induced by the presence, overabundance, persistence or activation of peripheral blood mononuclear cells, particularly eosinophils, or other cells of the immune system. For example, a pharmaceutical composition is therapeutically effective where a patient who has an immunological disorder, such as an eosinophil-associated disorder, has less severe or reduced symptoms when treated with the pharmaceutical composition compared with symptoms prior to said treatment. A pharmaceutical composition administered to a patient is also therapeutically effective where symptoms associated with an immunological disorder are prevented from occurring in a patient who has a history of such symptoms or who is considered likely to present with such symptoms.

In certain embodiments, a pharmaceutical composition useful in the methods of the invention may contain formulation materials for modifying, maintaining or preserving, for example, the pH, osmolarity, viscosity, clarity, color, isotonicity, odor, sterility, stability, rate of dissolution or release, adsorption or penetration of the compositions. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See REMINGTON'S PHARMACEUTICAL SCIENCES, 18th Edition, (A. R. Gennaro, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the Pin1 inhibitors of the invention.

In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions of the present invention comprise Tris buffer of about pH 7.0-8.5, or acetate buffer of about pH 4.0-5.5, and may further include sorbitol, sucrose, Tween-20 and/or a suitable substitute therefor. In certain embodiments of the invention, Pin1 inhibitor compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the Pin1 inhibitor product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired Pin1 inhibitor in a pharmaceutically acceptable vehicle. A particularly suitable vehicle for parenteral injection is sterile distilled water in which the Pin1 inhibitor is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used to promote sustained duration in the circulation. In certain embodiments, implantable drug delivery devices may be used to introduce the desired Pin1 inhibitor.

Pharmaceutical compositions of the invention can be formulated for inhalation. In these embodiments, Pin1 inhibitors are advantageously formulated as a dry, inhalable powder. In preferred embodiments, Pin1 inhibitor inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. Pin1 inhibitors that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the Pin1 inhibitor. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of Pin1 inhibitors in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving Pin1 inhibitors in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 22:547-556), poly(2-hydroxyethyl-methacrylate) (Langer et ale, 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (European Patent Application Publication No. EP 133,988). Sustained release compositions may also include liposomes that can be prepared by any of several methods known in the art. See e.g., Eppstein et al., 1985, *Proc. Natl. Acad. Sci. USA* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

Pin1 inhibitors useful in the methods of the invention can be admixed, encapsulated, conjugated or otherwise associated with other molecules, molecule structures or mixtures of compounds, for example, liposomes, receptor targeted molecules, oral, rectal, topical or other formulations, for assisting in uptake, distribution and/or absorption in a patient, using methods that are well known in the pharmaceutical arts.

The Pin1 inhibitors of the invention may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, flavoring and/or coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The Pin1 inhibitors of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Pin1 inhibitors of the invention may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas Examples of such dermal penetration enhancers include dimethylsulfoxide and related analogs.

The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the Pin1 inhibitors of this invention are ordinarily combined with one or more adjuvants appropriate to the indicated route of administration. If administered by mouth, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0,5 mg to about 14 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

Dosing frequency will depend upon the pharmacokinetic parameters of the particular Pin1 inhibitor used in the formulation. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In certain embodiments, Pin1 inhibitors can be administered to patients throughout an extended time period.

Pharmaceutical compositions and/or Pin1 inhibitors of the invention can be administered alone or in combination with other therapeutic agents, in particular, in combination with other immunosuppressive agents. For example, where the pharmaceutical composition or Pin1 inhibitor is used to prevent acute or chronic rejection of transplanted tissues or organs, the immunosuppressive agent can be cyclosporin A (CsA) or FK506 (Tacrolimus). As discussed in the Examples herein, the combination of a Pin1 inhibitor and an existing therapeutic agent, such as CsA, allows for use of suboptimal amounts (i.e. lower amounts as compared with traditional amounts used in transplantation therapy) of the existing therapeutic agent, thus providing lower toxicity to the patient.

The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

Unless otherwise required by context, singular terms used herein shall include pluralities and plural terms shall include the singular,

EXAMPLES

The following examples, including the experiments conducted and results achieved are provided for illustrative purposes only and are not to be construed as limiting the invention.

Example 1

The Effect of Peptidyl-prolyl Isomerase Inhibitors on Eosinophil Survival

Eosinophils (Eos) are typically present at low levels (1-2% of PBMC) in the blood of normal individuals and turnover rapidly with a lifespan of approximately 3 days. In asthma, Eos migrate into the lung where they can be found in the airways and parenchyma. In active asthmatics, Eos can comprise 50% of the total airway immune cells. After their removal by bronchoalveolar lavage (BAL), pulmonary Eos show markedly prolonged in vitro survival (>7 days) which can be attenuated with anti-GM-CSF antibodies. These cells also show evidence of generalized activation, including respiratory burst, cytokine expression and prostaglandin release.

Pulmonary eosinophilia is associated with pathological conditions such as asthma, based on their increased numbers and activation state in such disorders. Eosinophils are known to be activated, inter alia, by hyaluronic acid, and one of the hallmarks of activation is increased expression of a cytokine, GM-CSF (Esnault et al., 2002, Arch. Immunol. Ther. Exp (Warsz) 50: 121-130). Autocrine GM-CSF expression in turn promotes survival of eosinophils. Activation is also associated with changes in protein phosphorylation, which can be readily detected analytically. To characterize the mechanisms connecting hyaluronic acid (HA) activation to GM-CSF expression and eosinophil survival, GM-CSF mRNA decay was measured. These experiments showed that within several hours of HA treatment, GM-CSF mRNA was ~3 fold more stable, accounting for increased cytokine mRNA accumulation and ultimately, secretion. However, when the mitogen-activated protein kinase (MAPK) ERK was inhibited pharmacologically with PD98059, GM-CSF mRNA failed to accumulate. This effect occurred rapidly (within 10-30 minutes of addition of the inhibitor) and it was found that GM-CSF mRNA was destroyed at the rate characteristic of resting cells rather than in cells activated with HA. These effects occurred quickly, suggesting that ERK activity was continuously required for GM-CSF mRNA stabilization and that ERK mediated changes in GM-CSF mRNA decay reflected changes in the phosphorylation of proteins which participated in or regulated the decay process (since there was insufficient time for new protein synthesis).

The identity of those proteins was determined by comparing the pattern of phosphorylated proteins by 2-dimensional gel analysis after HA treatment with HA treatment in the presence of the MAPK ERK inhibitor, PD98059. To this end, peripheral blood was obtained by venipuncture from patients who had allergic rhinitis or asthma; patients were not symptomatic at the time blood was obtained. Peripheral blood eosinophils (Eos) were purified using a negative immunomagnetic procedure as described in Esnault and Malter (2001, J. Immunol. 166:4658-96). After isolation, Eos were maintained in vitro in RPMI 1640 medium (Gibco Life Technologies, Grand Island, N.Y.) with 10% fetal calf serum (Gibco Life Technologies, Grand Island, N.Y.) and 50 µg/ml gentamicin (Gibco Life Technologies, Grand Island, N.Y.) at 37° C. in 5% $CO_2$, and were metabolically labeled and activated by treatment under these culture conditions with 100 µg/ml HA (~5 hours total, see below). Viability of Eos ($1 \times 10^6$ cells/ml) was assessed by trypan blue exclusion using a hemocytometer and revealed >98% were alive during treatment.

Eos from multiple donors were preincubated with $^{32}$P-orthophosphate for 1 hour, treated for 4 hours with HA alone or 4 hours of HA treatment followed by 30 minutes of incubation with the ERK inhibitor PD98056. Approximately 700 µg of cytoplasmic protein from Eos treated under each condition were subject to isoelectric focusing, followed by separation based on molecular weight in 8-18% sodium dodecyl sulfate (SDS) polyacrylamide gradient gel (Amersham Pharmacia Biotech, Piscataway, N.J.). The gels were first analyzed by autoradiography and then stained with Coomassie G-250. Spots showing altered $^{32}$P content representing increased or decreased phosphorylation were sequenced by MALDI-MS to determine the identity of the protein at those positions in the gel. Five proteins showed significant decreases in phosphorylation related to HA treatment (shown in Table 1).

TABLE 1

Proteins dephosphorylated by PD98059

| Protein identified | Function(s) |
| --- | --- |
| Phosphoglycerate Kinase I | Glucose metabolism |
| Eosinophil-derived neurotoxin | Ribonuclease and neurotoxic activity |
| 30S ribosomal protein S1 | Protein translocation, RNA binding |
| KIAA1799 protein | Cell signaling, cell motility |
| PPIase, Cyclophilin A | Regulate cytokine production |

The peptidyl-prolyl isomerase (PPI) cyclophilin A (CYA) was particularly noteworthy because the CYA inhibitor, cyclosporin A (CSA) has been implicated in IL-2 and GM-CSF gene expression and eosinophil accumulation in bronchial biopsies (Schreiber and Crabtree, 1992, *Immunol. Today* 13:136-42; Khan et al, 2000, *Am. J. Respir. Crit. Care Med.* 162:1377-82). The PPI's cyclophilin A and FK506 binding protein catalyze cis-trans isomerization at phosphorylated amino acids (such as serine, threonine or other amino acid that immediately precede a proline residue). Pin1, the 3$^{rd}$ member of the mammalian PPIase family shows greater specificity, only isomerizing the peptide bond between phosphorylated serine or threonine residues immediately preceding a proline (Pro) residue {Ser/Thr-Pro}. Pin1 modulates the eukaryotic cell cycle by targeting proteins such as NIMA and Cdc25C and after isomerization, altering their interactions with other proteins. In the absence of Pin1 activity, cells are unable to progress through the cell cycle and accumulate in the $G_0$ phase.

Example 2

Pin1 Required for GM-CSF Release, GM-CSF mRNA Stabilization and Cell Survival The PPIase inhibitor cyclosporin A (CsA) has been implicated in the expression of GM-CSF by airway cells (Kita, H. et al. 1991, *J Exp Med.* 174: 745-748; Khan, L. N. et al. 2000, *Am J. Respir. Crit. Care Med.* 162:1377-1382) but the effects of juglone, a specific and irreversible Pin1 inhibitor (Hennig, L. et al. 1998, *Biochemistry* 37:5953-5960) are unknowns. Because secreted GM-CSF is essential for Eos survival in vitro, the effect of FK506, CsA and juglone on cell survival after activation with hyaluronic acid (HA) was evaluated. HA causes GM-CSF mRNA stabilization culminating in cytokine secretion (Esnault, S. & Malter, J. S, 2003, *J. Immunol.* 171: 6780-6787).

Purified peripheral blood Eos were incubated with HA alone or HA plus various concentrations of CsA, juglone or FK506 (all from Sigma Chemical Co., St. Louis, Mo.), and cell viability was determined at day 4. Consistent with previous results (Esnault, S. & Malter, J. S. 2003, *J. Immunol* 171: 6780-6787) the survival of control, untreated Eos was 5-20% (depending on the donor) which increased by 3-5 fold after HA treatment (FIGS. 1A and 1B). Anti-GM-CSF antibodies (obtained from Santa Cruz Biotech, Santa Cruz, Calif.) completely prevented enhanced survival (not shown) demonstrating HA induced GM-CSF secretion. CsA induced Eos cell death (~10% survival at 16 µM) as did juglone (5% survival at 0.1 or 1.0 µM) (FIGS. 1A and 1B) while FK506 had no effect. The mechanism of Eos death was evaluated by western blotting. As shown in FIG. 1C, activated caspase 3 (identified using antibodies obtained from Santa Cruz Biotech) was detected in control, untreated cultures but was absent after HA treatment. Treatment with juglone antagonized the protective effects of HA resulting in caspase 3 activation. Accordingly, these results indicate that, HA, via the induction of GM-CSF, prevented caspase mediated apoptosis. Conversely, inactivation of Pin1 with juglone caused caspase 3 activation and apoptosis in eosinophils.

This decreased survival could have reflected inhibition of GM-CSF secretion, blockade of GM-CSF receptor signaling or induction of apoptosis through a GM-CSF independent mechanism. To investigate the causes of decreased eosinophil survival associated with regulation of GM-CSF expression and activity, recombinant human (rh) GM-CSF (100 pg/ml) was added to Eos cultures in the presence of various concentrations of CsA and juglone and eosinophil survival determined at day 4 of culture. CsA induced Eos apoptosis despite activation with HA or GM-CSF. In contrast, GM-CSF was able to antagonize the apoptosis-promoting effects of juglone at low concentrations (0.1 µM, FIGS. 1A & 1B). These data suggested that Pin1 inhibition prevented GM-CSF release after HA treatment.

In order to assess this possibility, GM-CSF mRNA levels were measured by RT/PCR-Southern blot hybridization experiments. These results (shown in FIGS. 2A & 2B) demonstrated that HA treatment consistently increased GM-CSF mRNA levels by 2-4 fold in a manner that was unaffected by CsA at 1.6 µM or 16 µM. However, juglone treatment reduced GM-CSF mRNA to untreated control levels in a dose dependent fashion (FIGS. 2A & 2B). These data suggested that Pin1 was required for GM-CSF mRNA upregulation, cytokine secretion and enhanced Eos survival while CsA induced Eos apoptosis through a non-GM-CSF dependent mechanism.

It remained possible that juglone's effects were nonspecific. To demonstrate Pin1 specificity of the observed effect of juglone treatment, Eos were transduced with the WW domain of Pin1 fused to an N-terminal TAT penetratin tag. The WW domain functions as a dominant negative by blocking endogenous Pin1 activity (Lu et al., 2001, *J. Biol. Chem.* 277:2381-2384).

The results of these experiments are shown in FIG. 2C. When added along with HA, TAT-ww-Pin1 completely prevented GM-CSF mRNA upregulation (FIG. 2C), while the control construct (TAT-GFP) had no effect. Eos survival closely paralleled GM-CSF mRNA abundance with TAT-ww-Pin1 treated cultures that was indistinguishable from untreated, resting controls (FIG. 2D). However, augmentation of TAT-ww-Pin1 treated cultures with rhGM-CSF fully restored survival (FIG. 2D). These results indicated that Pin1 activity was necessary for HA-induced GM-CSF mRNA transcription and/or stability but not for the anti-apoptotic effects of GM-CSF itself.

It had been previously demonstrated that Eos activation with HA or TNF-α plus fibronectin reduced the rate of GM-CSF mRNA decay (Esnault and Malter, 2003, *J. Immunol* 166:4658-4663; Esnault and Malter 2003, *J. Immunol.* 171: 6780-6787). In view of this evidence and the rapid kinetics of GM-CSF mRNA clearance after juglone treatment (FIG. 2B), Eos were activated with HA or HA plus juglone prior to the addition of the transcriptional inhibitor actinomycin D and GM-CSF mRNA decay was determined by RT/PCR-Southern blot analysis. In the absence of juglone (HA alone), GM-CSF in RNA was extremely stable ($t_{1/2}$>80 min) (FIG. 2E). This stability decreased by >4 fold ($t_{1/2}$~21 min) after Pin1 blockade. These results demonstrated that Pin1 acted "downstream" from HA-mediated GM-CSF mRNA transcriptional activation and controlled cytokine secretion and cell survival by regulating GM-CSF mRNA decay.

Example 3

Pin1 Associated with AUF1 and is Rapidly Degraded After Juglone Treatment

In view of the results set forth in Example 2 above, it was evident that cytokine mRNA decay played a role in the effects of HA-activation of eosinophils and juglone inactivation of Pin1. Emerging data implicates AU-rich mRNA binding proteins (AREBPs) in the control of cytokine in RNA decay: both stabilizing and destabilizing AREBP's have been defined (Carballo et al., 2000, *Blood* 95:1891-1899; Fan et alt, 1998, *EMBO J.* 17:3448-3460; Capowski et al, 2001, *J. Immunol.* 167:5970-5976). The majority of AREBPs are phosphoproteins, of which many contain potential Pin1 recognition sites (Ser/Thr-Pro) (FIG. 6).

Thus, the possibility that Pin1 regulated GM-CSF decay through physical interactions with different AREBPs with subsequent modulation of binding activity or protein/protein interactions through phosphorylation-dependent, PPIase activity was investigated. To this end, Eos cytoplasmic extracts were immunoprecipitated using an anti-Pin1 antibody (obtained from Gary Brewer, Robt Wood Johnson Medical School, NJ) followed by immunoblot with anti-AREBP antibodies. These results are shown in FIG. 3A. Of the AREBPs detected, AUF1 and HuR were consistently co-precipitated with Pin1 (although the latter was barely detectable while the others were not detected under any circumstances). All 4 isoforms of AUF1 (p45, p42, p40 and p37) were coprecipitated with Pin1 (FIG. 3A) despite the presence of Pin1 isomerization sites ($Ser^{83}$-$Pro^{84}$) found only in p45 and p40 (Wilson et al., 2003, *J. Biol. Chem.* 278:33039-33048). Pin1 immunoprecipitated in the presence or absence of RNase, showing that p42 and p37 AUF1 associated with Pin1 via protein-protein interactions, possibly including the other AUF1 isoforms. Reverse immunoprecipitation with anti-AUF1 antibodies also precipitated Pin1. These observations indicated that Pin1 interacted with all AUF1 isoforms independent of GM-CSF or other ARE-containing mRNAs.

The effects of HA and juglone treatment on the interactions between AUF1 and Pin1 were then examined. Somewhat unexpectedly, HA had no effect on the amount of cytoplasmic Pin1 nor its binding to AUF1 (FIG. 3A), consistent with the presence of Pin1 binding sites in each isoform. However, juglone rapidly reduced both Pin1 and AUF1 levels although there was sparing of the p37 isoform (FIG. 3A). Indeed by 120 minutes of exposure to juglone, p45, p42 and p40 as well as Pin1 had essentially disappeared from the IP's, indicative of cytoplasmic clearance. Transduction of resting or HA-activated Eos with TAT-wwPin1 had no effect on Pin1 or AUF1 levels, suggesting that irreversible, enzymatic inhibition of Pin1 by juglone induced degradation of both proteins.

Although the intracellular site of Pin1 catabolism is unknown, it was known that AUF1 is degraded in the proteosome. Proteasomal degradation is very rapid and could account for the observed kinetics of Pin1 and AUF1 loss observed after juglone treatment. To address this possibility, Eos were exposed to the proteasome inhibitor MG132 (4 h) (Sigma) and juglone (10 min before harvest) and lysates immunoblotted. As shown in FIG. 3C, juglone-induced p45, p42 and p40 AUF1 degradation was completely blocked upon MG132 treatment. At higher MG132 concentrations, AUF1 accumulated to levels greater than those detected in untreated cells, suggesting normal catabolism of this protein occurred in the proteasome. Under these conditions, MG132 only partially prevented Pin1 degradation, which indicated that Pin1 was degraded through another cellular proteolytic system(s).

Steady state GM-CSF mRNA levels (as shown in FIGS. 2A-2E and FIG. 3D) were analyzed in eosinophils and the results showed that juglone antagonized HA-mediated increases in GM-CSF mRNA. Based on data shown above (FIGS. 2A-2E), this likely reflects accelerated GM-CSF mRNA decay. However, MG132 antagonized juglone-induced decreases of GM-CSF mRNA (FIG. 3D) but had no observable effect when the cells were treated with MG132 alone. These data were consistent with prior observations that ARE mRNA decay requires proteasome activity (Laroia et al., 2002, *Proc. Natl Acad. Sci. U.S.A.* 99:1842-1846). As transcription of many mRNAs was unaffected by prolonged treatment of cells with MG132 (Ciechanover, 1998, *EMBO J.* 17:7151-7160), the observed enhanced GM-CSF mRNA levels presumably reflected GM-CSF mRNA stabilization.

Example 4

Pin1 Regulated the Interaction of AREBPs with GM-CSF mRNA

AUF1 has been shown to bind GM-CSF mRNA in multiple cell types. Paradoxically, binding has been associated with both stabilization and destabilization of ARE mRNAs (Bhattacharya et al., 1999, *Nucleic Acids Res.* 27: 1464-1472; Sarkar et al., 2003, *Mol. Cell Biol.* 23:6685-6693). The partitioning of GM-CSF mRNA with AUF1 was evaluated in resting Eos, after HA activation or HA plus Pin1 inhibitors. RT-PCR/Southern blot analysis of anti-AUF1 immunoprecipitation pellets showed a substantial percentage of cellular GM-CSF mRNA associated with AUF1 in resting cells (FIG. 4A, right) that was dramatically reduced after HA treatment A brief exposure to juglone (10 min, FIG. 4A, left) or TAT-wwPin1 had little effect on GM-CSF mRNA steady state levels (FIG. 4A, left) but caused reassociation of GM-CSF mRNA with AUF1 (FIG. 4A, right). Slightly longer exposure to juglone (15-30 min) (FIG. 2B) or to TAT-wwPin1 (30 min) (FIG. 4B) further increased the amount of GM-CSF mRNA bound to AUF1, while steady state GM-CSF mRNA amounts rapidly decreased to those seen in resting cells (not shown and FIGS. 2A & 2C). Together, these observations suggested that AUF1-GM-CSF mRNA interactions triggerred rapid decay in resting cells. HA-mediated cell activation was capable of preventing this interaction but only if Pin1 was enzymatically functional. This mechanism is consistent with the idea that HA induced Pin1-mediated isomerization of AUF1 with loss of its mRNA binding activity.

Given the propensity of cytoplasmic mRNAs to be associated with protein, experiments were designed to determine if another protein replaced AUF1 after HA treatment. One possibility was hnRNP C, which shows increased binding to GM-CSF mRNA after Eos activation (Esnault and Malter, 2003, *J Immunol.* 171: 6780-6787). Therefore, anti-hnRNP C (Sigma) immunoprecipitates of cytoplasmic extracts were examined for GM-CSF mRNA by RT-PCR/Southern blot hybridization analysis. Consistent with previous observations (Esnault et al, 2003, *J. Immunol.* 171: 6780-6787), HA treatment induced a rapid increase in GM-CSF mRNA binding to hnRNP C (FIG. 4B). Incubation of cells with TAT-wwPin1 rapidly reduced GM-CSF mRNA associated with hnRNP C and increased GM-CSF mRNA association with AUF1. HuR, while present, did not associate with GM-CSF mRNA under any conditions, and the association of Pin1 and AUF1 was unaffected by HA (FIG. 3A) or TAT-wwPin1. In addition, hnRNP C did not co-precipitate with anti-Pin1 antisera. These data suggested that in the absence of Pin1 activity, either in resting cells (Pin1 is less active after phosphorylation, FIG. 5A; Lu et al., 2001, *J. Biol. Chem.* 277: 2381-2384) or after TAT-wwPin1 treatment, AUF1 displaced hnRNP C and bound to GM-CSF mRNA, leading to its degradation. After HA treatment, this process was reversed resulting in GM-CSF mRNA stabilization.

Example 5

HA Altered the Phosphorylation of AUF1 and Pin1

Figure 5:
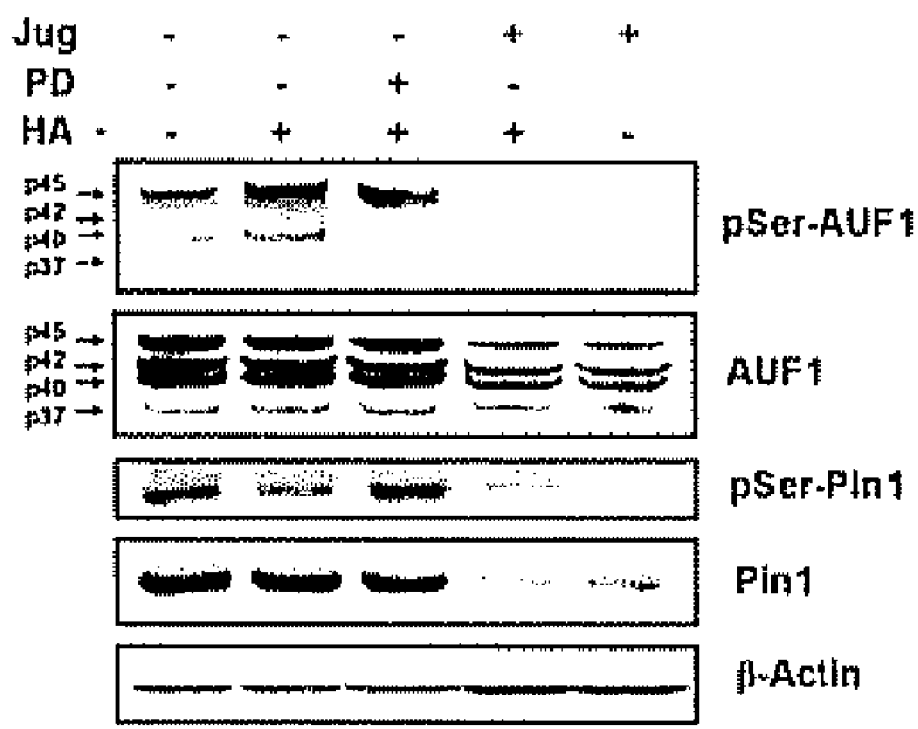
FIG. 5 shows that p45 and p40 AUF1 were phosphorylated, which was consistently increased by HA treatment and partially antagonized by PD98059, an Erk inhibitor in resting cells. Cells were untreated (−/−/−), treated with HA alone (4 h), HA (4 h) plus juglone (1 μM added 10 min before harvest) or HA plus Erk inhibitor PD98059 (PD) (50 μM added 30 min before harvest). Cytoplasmic extracts were immunoblotted with anti-phosphoserine, anti-AUF1 or anti-Pin1 antibody as shown.

As the association of Pin1 and AUF1 was unaffected by HA (FIG. 2A) despite the loss of GM-CSF mRNA from the protein complex (FIGS. 4A & 4B) it was hypothesized that either AUF1 and/or Pin1 was modified by HA mediated signaling. Phorbol esters trigger the dephosphorylation of $Ser^{83}$ and $Ser^{87}$ of p40 AUF1 was concomitant with the stabilization of IL-1β and TNF-α mRNAs (Wilson et al. 2003, *J. Biol. Chem.* 278:33029-33038). Therefore, cytoplasmic extracts from control or HA-treated Eos were immunoblotted with anti-phosphoserine, anti-AUF1 or anti-Pin1 antibodies. In resting cells, p45 and p40 AUF1 were phosphorylated, which was consistently increased by HA treatment and partially antagonized by PD98059, an Erk inhibitor (FIG. 5). HA treatment reproducibly dephosphorylated Pin1, which has been shown to increase its isomerase activity (Lu et al., 2001, *J. Biol. Chem.* 277:2381-2384). In addition, Pin1 showed >1000-fold more activity towards $pSer^{83}$-Pro than the unphosphorylated substrate (Yaffe et al., 1997, *Science* 278:1957-1960). These data suggested that the observed combination of Pin1 and AUF1 post-translational modifications induced by HA would result in AUF1 isomerization with loss of binding to GM-CSF mRNA.

Example 6

Pin1 and the Regulation of Cytokine mRNAs in PBMC and T Cells.

Figure 7:
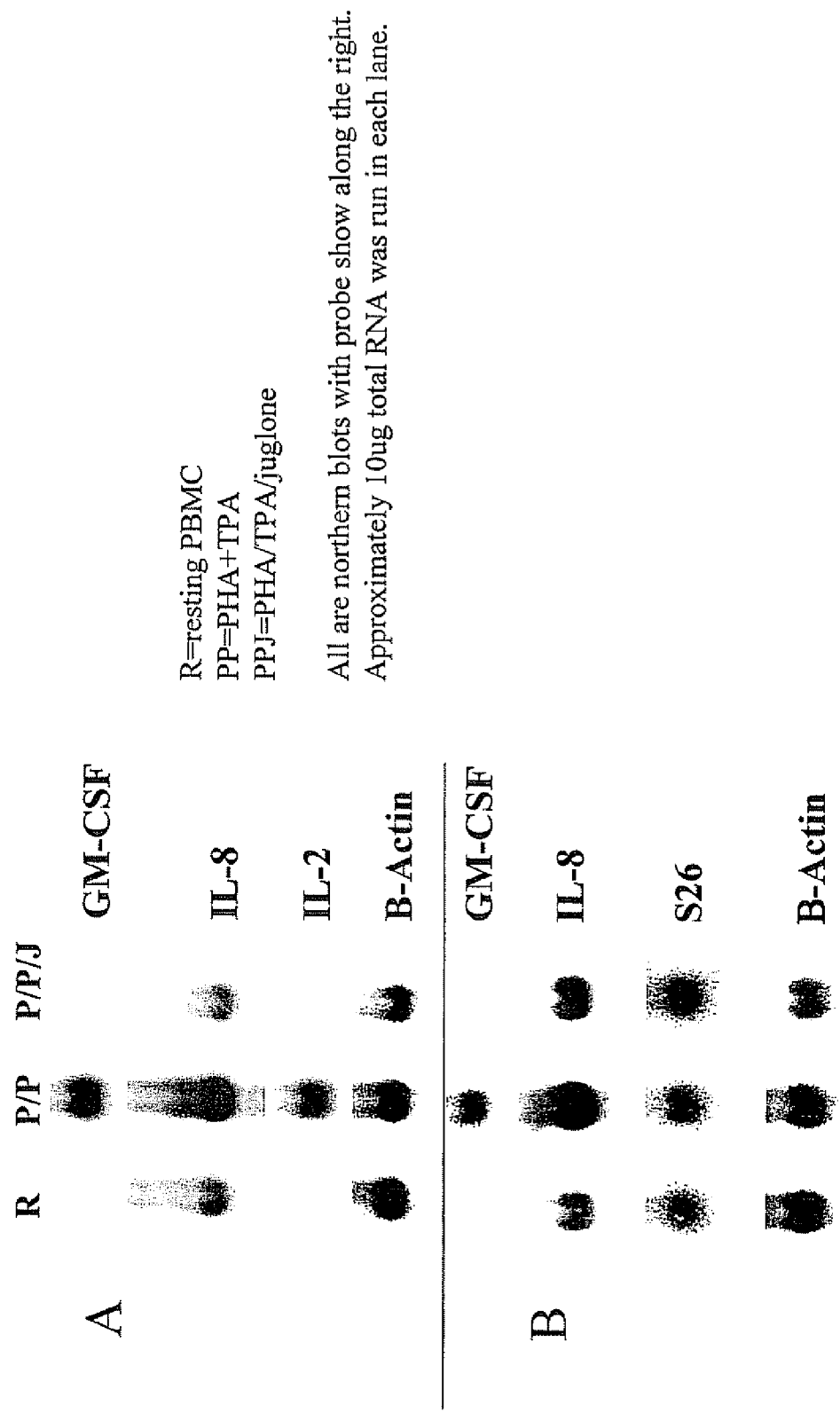
FIG. 7 shows Pin1 blockade with juglone prevented cytokine mRNA accumulation by peripheral blood mononuclear cells (PBMCs). PBMCs were isolated from healthy donors by Percoll® gradient centrifugation of heparinized whole blood. Cells were cultured in RPMI 1640 media supplemented with 10% fetal calf serum (FCS) at $1 \times 10^6$ cells/ml prior to the addition of PMA (20 ng/ml) and PHA (5 ug/ml) (P/P) or PMA, PHA and juglone (1 uM) (P/P/J); "R" designates the control lane without addition of additional substances. After 4 h, cells were lysed and 10 ug of recovered RNA northern blotted and hybridized with probes shown along the left side of the Figure. "A" and "B" refer to results with 2 different donors.
Figure 8:
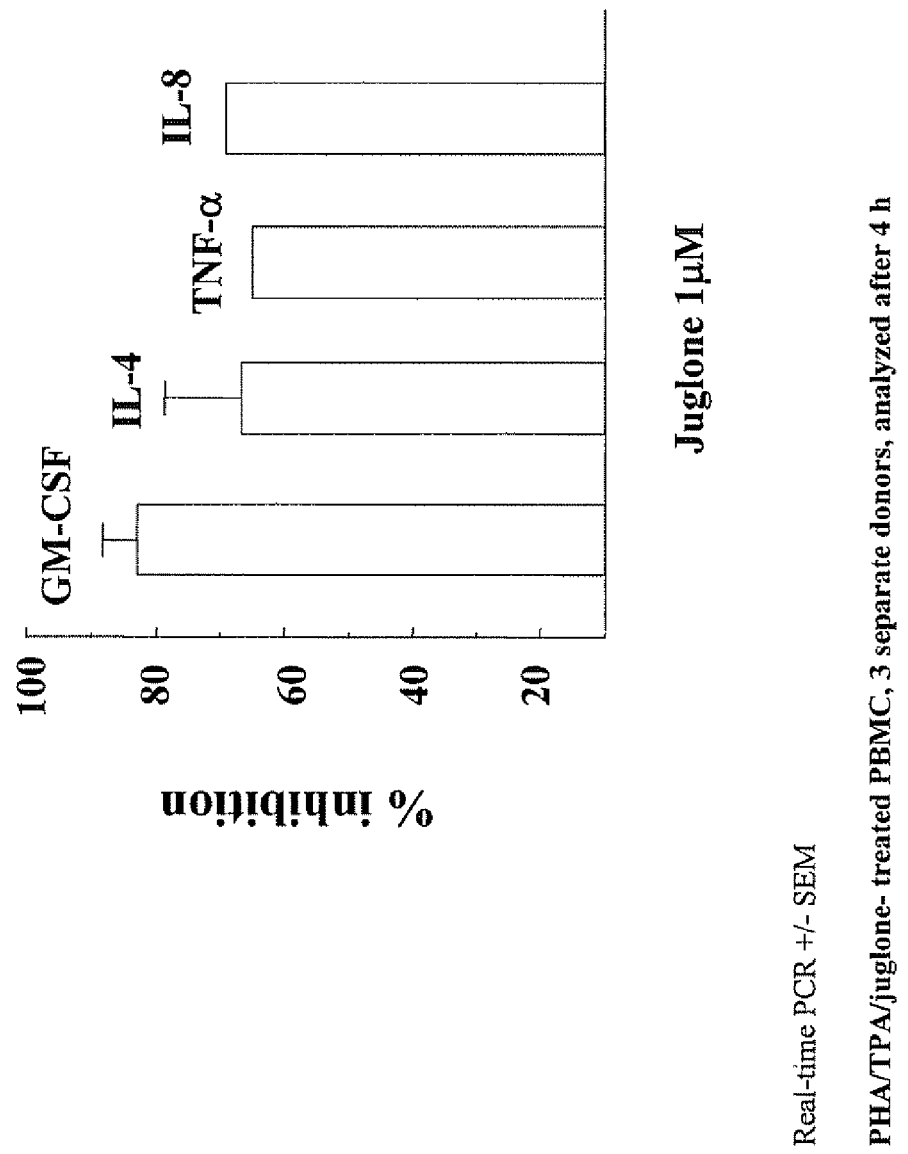
FIG. 8 shows that juglone inhibited cytokine mRNA accumulation by PBMC, PBMC were prepared as described in FIG. 7 above from 3 donors and treated with PHA/PMA (as in FIG. 7) plus or minus juglone (1 μM). After 4 h, RNA was isolated from the cells and used for quantitative PCR (qPCR) for the cytokine mRNAs shown. Data are presented as % inhibition in samples with juglone.
Figure 9:
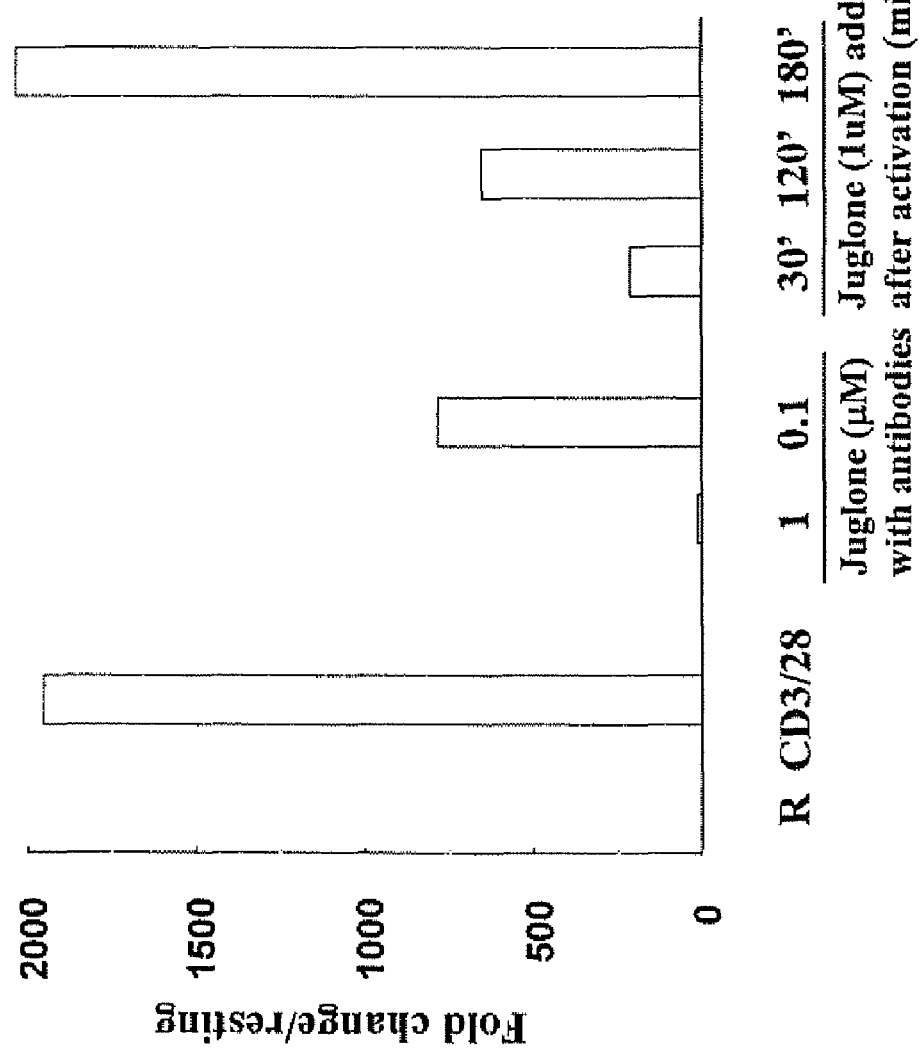
FIG. 9 shows that Pin1 inhibition prevented purified T cells from accumulating GM-CSF mRNA after activation with mitogenic antibodies. Purified T cells were prepared by negative selection of PBMC (T cells>98% pure based on flow cytometry) and activated with a combination of anti-CD3 and anti-CD28 antibodies. Juglone was added at 0.1 or 1 μM as shown along with the antibodies or at various times (as shown) at 1 μM after the antibodies. After 4 hours total incubation time, cells were lysed and mRNA used for RT-qPCR for GM-CSF mRNA, "R" refers to control untreated cells and the data has been normalized to these results.
Figure 10:
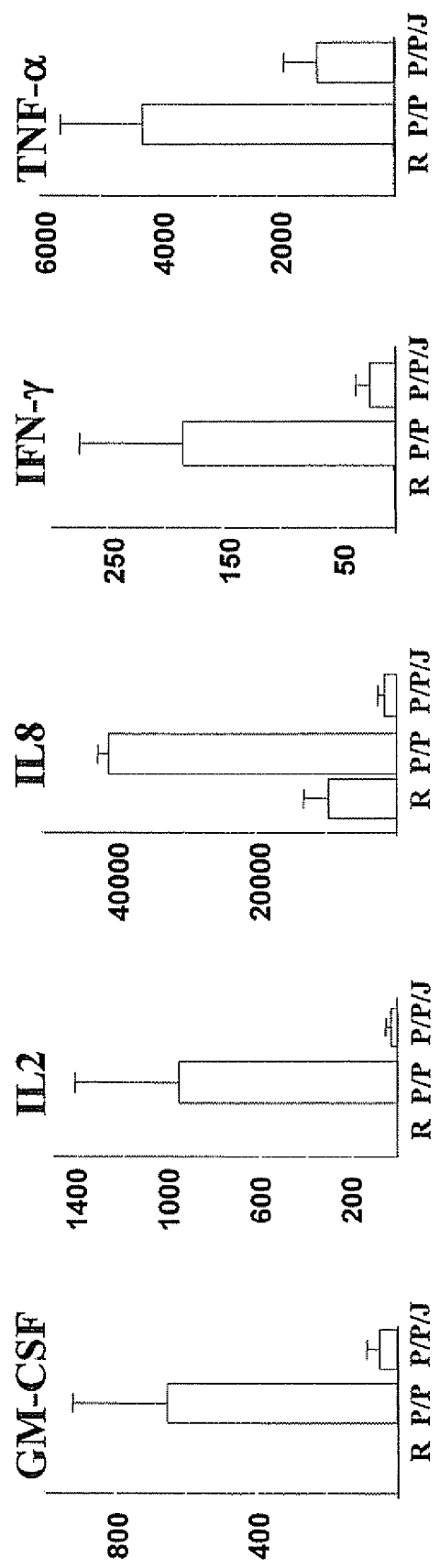
FIG. 10 shows that Pin1 inhibition prevented cytokine secretion by activated PBMC. PBMC were prepared as described above and cultured at $1 \times 10^6$ cells/ml in RPMI 1640 with 10% FCS. "R" refers to cultures with no additions (controls), "P/P" denotes cells stimulated with PMA and PHA (as above) (P/P) or PMA, PHA and 1 uM juglone (P/P/J). Supernatants were harvested after 4 hours and analyzed by ELISA for the cytokines shown. All "Y" axes are expressed in pg/ml cytokine.

The data above clearly implicated Pin1 in the regulation of GM-CSF mRNA stability and cytokine secretion by activated Eos, which provided an important insight into the pathogenesis of asthma. These observations suggested that Pin1 might control the production of other cytokines by other immune cells. Thus peripheral blood mononuclear cells (~70% T cells, 20% B cells, 5-10% macrophages/monocytes, obtained by phlebotomy of normal donors) were incubated with optimal concentrations of mitogens (phorbol ester (20 ng/ml), and PHA (40 ug/ml), both from Sigma) and cytokine in RNA levels were measured by northern blot or real time RT/PCR (qPCR) and cytokine secretion by ELISA. Blood cells were prepared from heparinized whole blood that was diluted in media, and PBMC isolated by Percoll gradient as described (Sedgwick et al., 2003, *Am J Respir Cell Mol Biol* 29:702-9). IL-2, IL-8, TNFα, IFNγ and GM-CSF mRNAs were evaluated first, since these cytokines all share 3' UTR AU-rich elements with GM-CSF. With the exception of IL-8, these mRNAs were undetectable in resting cells by northern blot (FIG. 7). However, within 4 hours of mitogenic stimulation cytokine expression increased dramatically. In contrast, when PBMC were mitogenically stimulated in the presence of 1 uM juglone, cytokine mRNA accumulation was almost completely blocked (FIGS. 7, 8), while juglone treatment 2 hours after stimulation had a partial effect (FIG. 9). By qPCR analysis, cytokine mRNAs that increased by between 1000 and 5000 fold within 4 h were typically suppressed by 65-90% by juglone treatment (FIGS. 8, 9). ELISA (FIG. 10) revealed a proportional reduction in cytokine release after Pin1 inhibition, demonstrating the importance of mRNA accumulation for cytokine synthesis.

Figure 11:
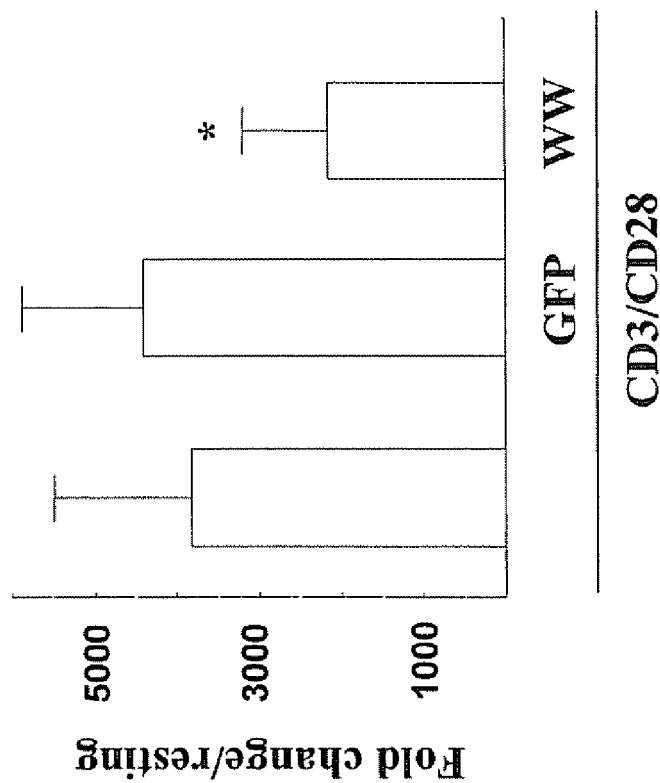
FIG. 11 shows that dominant negative Pin1 WW peptide blocked GM-CSF mRNA accumulation in PBMC, PBMC from 4 donors were activated with mitogenic anti-CD3 and anti-CD28 antibodies as described in FIG. 10 above. At the time of antibody addition, 20 nM of TAT-ww-Pin1 or TAT-GFP was added to the cells. At 4 hours, RNA was isolated and subjected to RT-qPCR for GM-CSF mRNA. * denotes results having a statistical significance of p<0.05 between TAT-ww-Pin1 treated cultures compared to either GFP-treated or control activated cells.

In order to confirm that Pin1 inhibition and not a secondary event nonspecifically influenced by juglone was responsible for the mRNA accumulation described above, PBMC were incubated with TAT-wwPin1 peptide at the same time as PMA/PHA activation. Compared to control cells treated with TAT-GFP, cytokine mRNA levels were reduced by 50-60% (FIG. 11). Therefore, PinI activity was required for the accumulation of multiple cytokine mRNAs after PMA/PHA stimulation of PBMC.

The effects of a more physiologic agonist were evaluated to determine if it could be similarly inhibited by Pin1 blockade. PBMC were incubated with anti-CD3 and anti-CD28 antibodies with or without juglone for 4 hours prior to harvest and qPCR. As seen with PMA/PHA, Pin1 inhibition prevented cytokine mRNA accumulation as well as secretion (FIG. 9), and similar data were obtained if TAT-wwPin1 was used in place of juglone. Therefore, Pin1 is a key intermediate which modulates T cell receptor and CD28 co-stimulatory signaling and whose activity was required for cytokine mRNA accumulation and cytokine release from activated immune cells.

Figure 12:
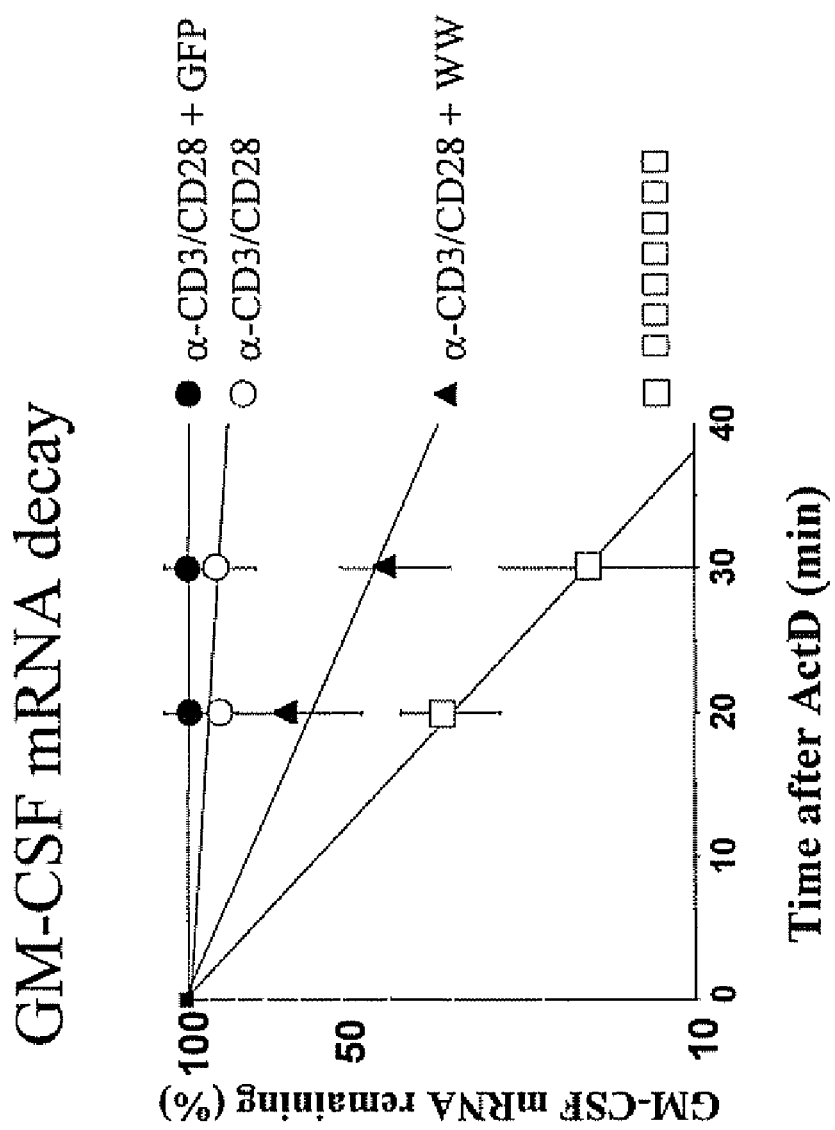
FIG. 12 shows that dominant negative Pin1 Peptide (TAT-ww-Pin1) destabilized GM-CSF mRNA. PBMC were cultured without additions (resting), activated with mitogenic antibodies alone as described above in FIG. 11 (CD3/CD28), with antibodies plus TAT-GFP (20 nM) (CD3/CD28+GFP) or plus TAT-ww-Pin1 (20 nM) (CD3/CD28+WW). After 4 h, actinomycin D (actD; 5 µg/ml) was added to block RNA transcription and cells harvested for RNA isolation and RT-qPCR for GM-CSF mRNA at the times shown. Data is plotted normalized to the amount of GM-CSF mRNA present at the addition of actD.

Based on the above data with eosinophils, it was hypothesized that Pin1 blockade destabilized cytokine mRNAs. Therefore, PBMC were incubated with mitogenic antibodies and TAT-wwpin1 or TAT-GFP for 4 hours. At that time, actinomycin D (actD, Sigma) was added to block further transcription and GM-CSF mRNA decay measured by qPCR. As shown (FIG. 12), GM-CSF mRNA was extremely stable in PBMC after mitogenic stimulation with or without TAT-GFP. In unstimulated cells, GM-CSF mRNA was very labile. Cells incubated with mitogens plus TAT-ww-Pin1 showed nearly as rapid GM-CSF mRNA decay as unstimulated controls. Therefore, as in eosinophils, Pin1 modulates activation dependent stabilization of cytokine mRNA by PBMC.

Figure 13:
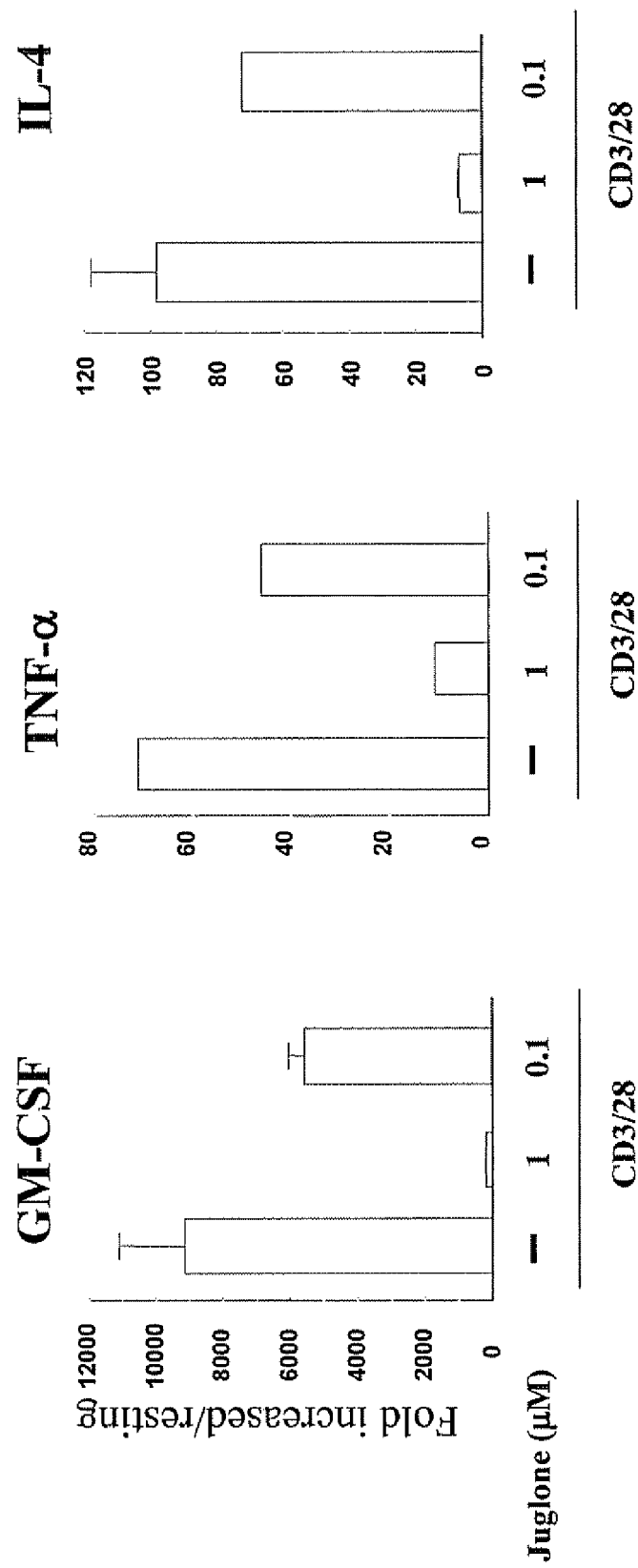
FIG. 13 shows that Pin1 inhibition prevented purified T cells from accumulating GM-CSF, IL-4 or TNF alpha mRNA after activation with mitogenic antibodies. Purified T cells were prepared by negative selection of PBMC (T cells>98% pure based on flow cytometry) and activated with a combination of anti-CD3 and anti-CD28 antibodies. Juglone was added at 0.1 or 1 µM as shown along with the antibodies. After 4 hours total incubation time, cells were lysed and mRNA used for RT-qPCR for the cytokine mRNAs shown "−" refers to control cells activated but not exposed to juglone.

As PBMC are heterogeneous, this cell population was fractionated into T cells by negative selection (as described in Sedgwick et al., 2003, *Am J Respir Cell Mol Biol.* 29:702-9). Typically this resulted in cultures of >98% pure, CD3 positive T cells. These were then activated with anti-CD3 and anti-CD28 antibodies (obtained from Santa Cruz Biotech), and the effects of Pin1 blockade on cytokine gene expression assessed by qPCR. As shown (FIG. 13), purified T cells showed strong activation after anti-CD3/anti-CD28 treatment and had between 1500- and 5000-fold increases in GM-CSF mRNA levels by 4 hours. Juglone (1 µM) added along with antibody reduced GM-CSF mRNA by between 80-95%. Based on PI/annexin staining and flow cytometry, activated T cells showed equivalent viability to those which were not activated.

The accumulation of ARE containing cytokine mRNAs that are related to T cell activation and migration was also examined by real tine PCR in splenocytes. Bulk rat splenocytes were activated in vitro with ionomycin/PMA (I/P) or I/P plus different concentrations of juglone as follows $5 \times 10^5$ spleen cells from normal WYK rats were cultured for 48 hours without or with ionomycin plus PMA (I/P), without or with juglone 1 µM (I/P/J1) or 0.1 µM (I/P/J0.1). IL-2 (2 ng/ml) was also added after 24 hrs to indicated cultures. After 48 hrs, the cultures were further supplemented with BrdU, juglone (1 or 0.1 µM) and IL-2 (2 ng/ml) as indicated. The proliferation was monitored after 18 hrs incubation with 5'-bromo-2'-deoxyuridine (BrdU) by a calorimetric assay (450 nm) as recommended by the manufacturer (Amersham, Piscataway, N.J.).

As expected, resting cells expressed low levels of IFN-γ, IL-2, TNF-α, and TGF-β mRNAs (FIG. 14A). After 4 hours of I/P, cytokine mRNAs increased by as little as 2 fold (TGF-β) to >500 fold (IL-2 and IFN-γ). Juglone (1 μM) completely blocked the accumulation of I/P-induced IFN-γ and IL-2 in RNAs, significantly reduced the level of TNF-α mRNA, and reduced TGF-β and CXCL-10 mRNA below resting levels. At lower juglone concentrations (0.1 μM), only the accumulation of IFN-γ mRNA was significantly inhibited whereas IL-2, TNF-α, CXCL-10 (IP-10) and TGF-β mRNAs were largely unchanged from I/P activated cells. These data suggested a variable sensitivity to Pin1 inhibition but confirmed that Pin1 regulated the production of diverse cytokine mRNAs by resting or activated rat splenocytes.

Cytokine elaboration was measured by control, activated or juglone treated activated splenocytes as follows. IFNγ secretion by splenocytes was evaluated by ELISPOT (R&D Systems, Minneapolis, Minn.) as described by the manufacturer. Triplicates of serial dilutions of cells were cultured with PMA (10 ng/ml) plus iononycin (1 μM) for 48 hours. The concentration of IFN-γ and IL-2 in the BAL fluid was determined using an ELISA kit (R&D Systems).

Consistent with the steady state mRNA levels, ELISA revealed dramatic reductions in IFN-γ and IL-2 secretion by juglone treated I/P stimulated spleen cells. As for mRNA, cytokine secretion showed a dose dependent response to juglone with maximal effects at 1 μM (FIG. 14B). The failure to produce cytokines was not a function of cell death as equivalent levels of apoptosis were observed in I/P versus I/P/juglone treated splenocytes (FIG. 14C). Based on BrdU incorporation, juglone (1 μM) effectively suppressed DNA synthesis despite the addition of exogenous IL-2 (FIG. 14D). Therefore, Pin1 blockade suppressed proliferation as well as the elaboration of proinflammatory cytokines by activated rat splenocytes.

Example 7

Role of Pin1 in Lung Transplant Rejection

The identification of Pin1 as a key signaling molecule required for cytokine elaboration suggested it might be a valuable target for immunosuppression in the context of organ transplantation. Therefore the ability of Pin1 inhibition to prevent rejection of an orthotopic lung allograft into a Class I HLA mismatched rat was tested. This is a well established rodent model where the entire left lung of a F344 rat is transplanted and reconnected via cuffs in the recipient WKY rat (Mizobuchi et al., 2004, *J Heart Lung Transplant.* 23:889-93). Thus the transplant was both ventilated and revascularized, while the endogenous tight lung remained in the recipient. In the absence of immunosuppression, the organ underwent very rapid and profound rejection within 3-4 days (R. Braun, UW Dept of Surgery, personal communication). By 3 days, the exterior surface was grossly hemorrhagic and decreased in volume, and histopathologic examination showed intense cellular infiltrate composed of PMNs, lymphocytes and macrophages, obliteration of alveoli and fibrosis.

To determine whether juglone had any effect on transplanted lung tissue in this model system, animals were dosed at 1 mg/kg juglone IP (dissolved at 10-20× in ethanol or chloroform, diluted to 1× in normal saline immediately prior to injection) on the day of surgery as well as each subsequent day thereafter. In some experiments, doses were split and delivered twice a day. On day 8, animals were sacrificed, bronchoalveolar lavage (BAL) performed on both lungs followed by inflation with 4% formalin for fixation. After 2 days, sections were cut from paraffin embedded blocks and stained with H&E. Other organs were also harvested including spleen and peripheral blood. As shown in FIG. 15, control transplants analyzed on day 8 showed typical rejection with massive inflammatory cell infiltrate, necrosis and complete alveolar loss and fibrotic scarring. Juglone-treated animals showed consistent and reproducible pulmonary sparing (FIG. 16). The alveoli in lung tissue from juglone-treated animals were largely intact (although occasional large, round cells, likely to be macrophages, were observed in small airspaces). Perivascular and peribronchial lymphoid aggregates were also present in tissue from juglone-treated animals, but neutrophils were largely absent and inflammation did not extend into the alveoli. Virtually identical data were obtained in six of eight transplanted rats who received juglone; the two failures were early in these studies and likely reflected drug insolubility. These data demonstrated for the first time that Pin1 was required for transplant rejection and suggested this PPIase as an alternative therapeutic target for immunosuppression. Although Pin1 is a cyclophilin, it does not interact with calcineurin (as does cyclophilin A), making it possible that CsA and Pin1 blockade could be additive or synergistic.

Figure 17:
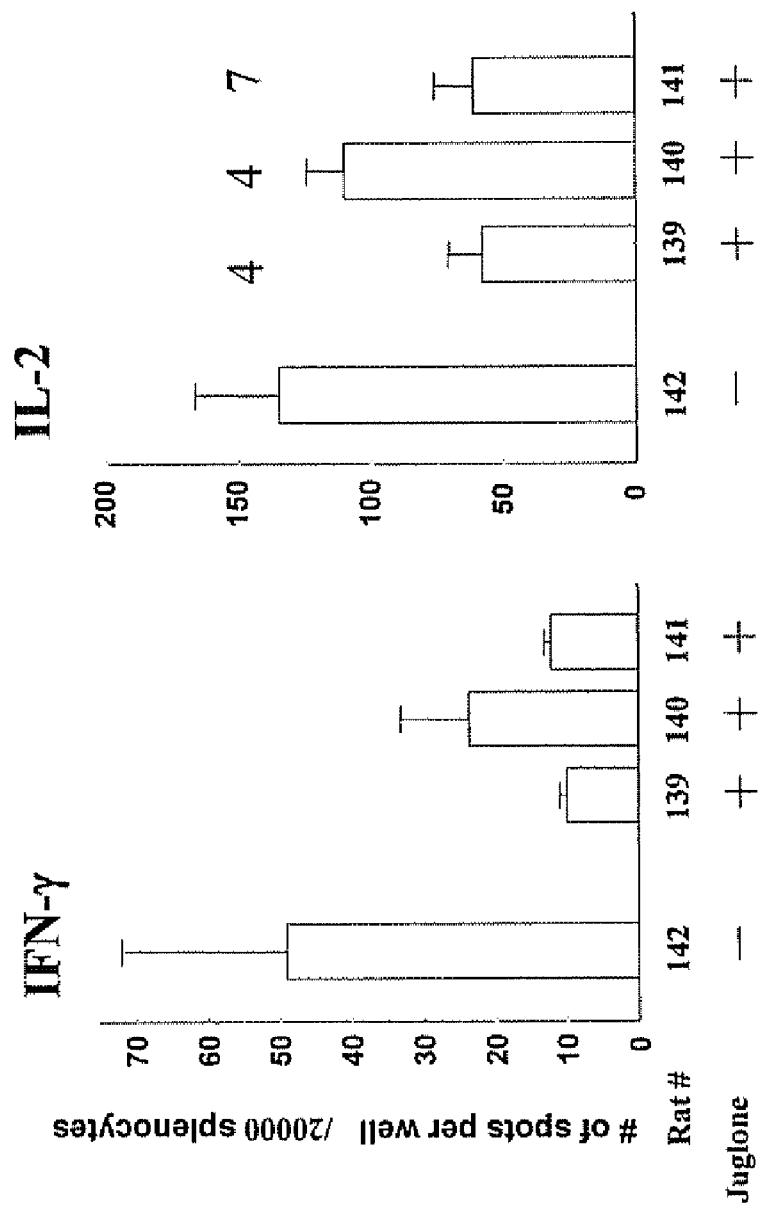
FIG. 17 shows that splenocytes from juglone-treated transplant recipients showed significantly fewer interferon (IFN-γ) and interleukin-2 (IL-2) producing colonies than splenocytes from transplanted animals not treated with juglone. Splenocytes (2000) from control or juglone-treated transplant recipients were activated with ionomycin (1 µM) and PMA (20 ng/ml) for 3 days prior to addition of anti-IL-2 or IFN gamma antibodies and color development and counting.
Figure 18:
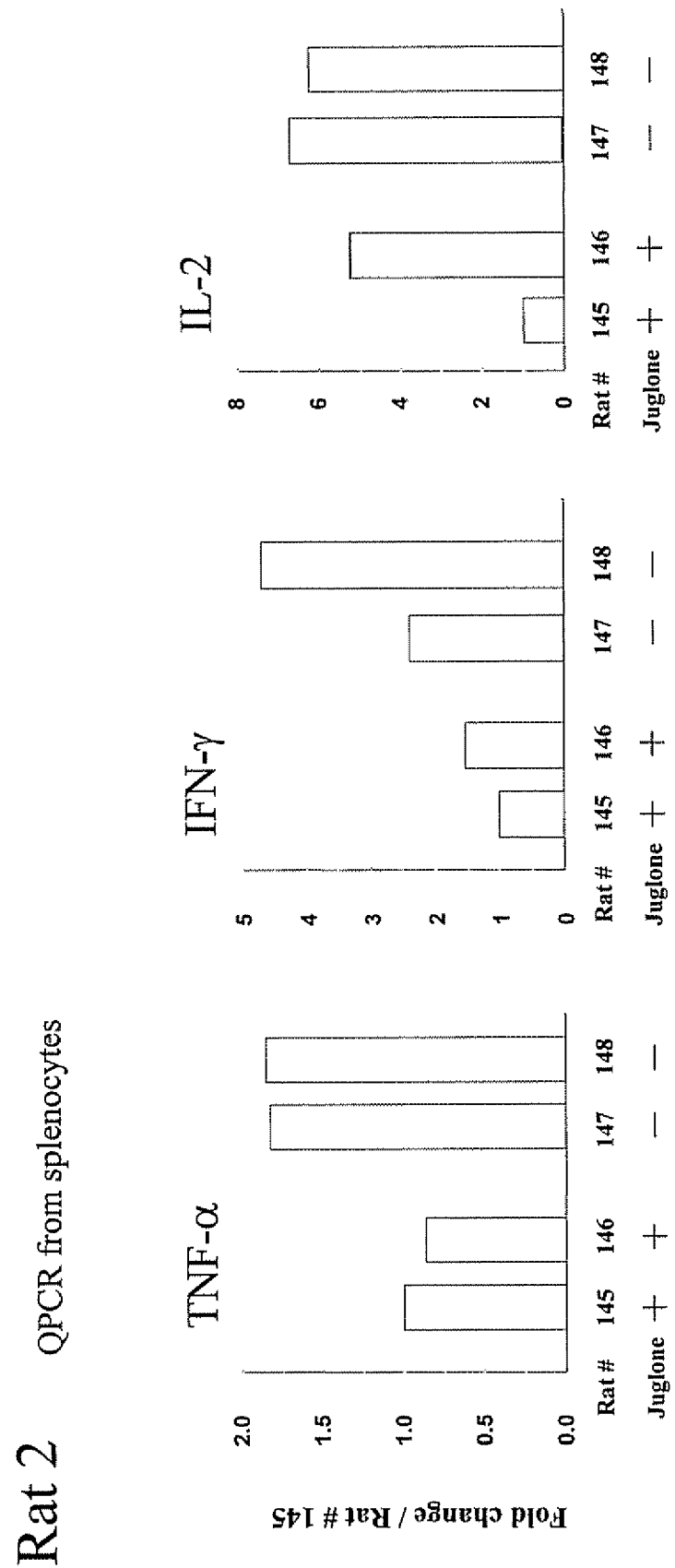
FIG. 18 shows that splenocytes from juglone-treated transplanted animals showed significantly reduced IL-2, IFN gamma and TNF alpha mRNA levels. Spleens were processed 8 days after transplantation from untreated or juglone-treated rats for mRNA isolation and RT-qPCR for IL-2, IFN or TNF alpha. Juglone treated mRNA levels were set to 100% in these analyses.

Next, immunologic changes between control and juglone treated transplant recipients were analyzed. After 1 week of Pin1 inhibition, the absolute counts and ratios of peripheral blood CD4+, CD8+ cells, as well as γ/δ lymphocytes were largely unaffected. Splenocytes harvested from control versus untreated animals (8 days after transplant) were stimulated with optimal concentrations of PMA (20 ng/ml) and ionomycin (1 μM) and analyzed by Elispot for IL-2 and IFNγ expression. As shown (FIG. 17), the number of cells expressing these cytokines was significantly reduced by approximately 60-70%. RT-PCR analysis on whole spleen showed significant changes in TNF-α, IL-2, and IFNγ mRNA levels, consistent with the Elispot data (FIG. 18). BAL from treated animals showed 50% fewer total cells than untreated controls although the absolute numbers remained above those in the untransplanted contralateral lung. RT-PCR for IL-2 and IFN-gamma of the lungs from juglone-treated animals showed about 35% of the IL-2 and IFN-gamma mRNA compared with the no treatment controls. These data suggested that some inflammation occurred despite Pin1 blockade. This may be a tolerizing or suppressive response (i.e. it is composed of CD8+ suppressors or T reg cells). These results indicated that blockade of Pin1 prevented allo-immune responses and conditions associated with immune cell activation, and recruitment with subsequent tissue damage, and thus that Pin1 inactivation was a target for immunosuppressive therapy.

Pin1 Inhibition Prevented Acute and Chronic Rejection

The cytokines and chemokines regulated by Pin1 have been extensively linked to the immunological and pathological events after organ transplantation. In addition, Pin1 is a member of the PPIase family of enzymes that also includes CyA and FKBP12. As interference with these cyclophilins with cyclosporin A and FK506, respectively, are the current mainstays of clinical immunosuppression after organ transplantation, we evaluated if Pin1 blockade had similar effects on organ rejection. We used the widely employed and strongly immunogenic rat orthotopic, single left lung transplantation model (Haque et al., 2002, *J. Immunol.* 169:1542-1549; Sekine et al., 1997, *J. Immunol.* 159; 4084-4093. The donor organ is attached via cuffs to the recipient's bronchial and vascular systems permitting normal function. The recipient (WKY) differs by a Class I MHC antigen from the donor (F344). Therefore, non-immunosuppressed animals experience profound acute rejection within several days and chronic rejection with alveolar, pleural, and peribronchial collagen deposition, loss of viable pneumocytes and eventual organ loss within 1-2 weeks.

The effects of a daily, single intraperitoneal (IP) injection of 1 mg/kg juglone on lung transplant rejection were evaluated. The orthotopic transplantation of left lung was performed as previously reported using the cuff technique (Mizuta et al., 1991, *J. Thorac. Cardiovasc. Surg.* 102:159-160; Mizuta et al, 1989, *J. Thorac. Cardiovasc. Surg.* 97:578-581). Briefly, rats were anaesthetized by inhalation of a mixture of isoflurane and oxygen, intubated and ventilated with a mixture of isoflurane and oxygen to maintain anesthesia. The donor rat was placed in a supine position and the heart and lungs were removed en bloc. The left lung was resected and the pulmonary vein, bronchus, and pulmonary artery were passed through teflon cuffs and the proximal ends were everted over the cuffs. On the recipient rat a left thoracotomy was performed. The donor pulmonary vein, bronchus, and pulmonary artery were inserted into the corresponding recipient hilar structures, and fixed with separate circumferential ligatures of silk. The chest wall was closed, and the isoflurane was stopped.

Figure 19:
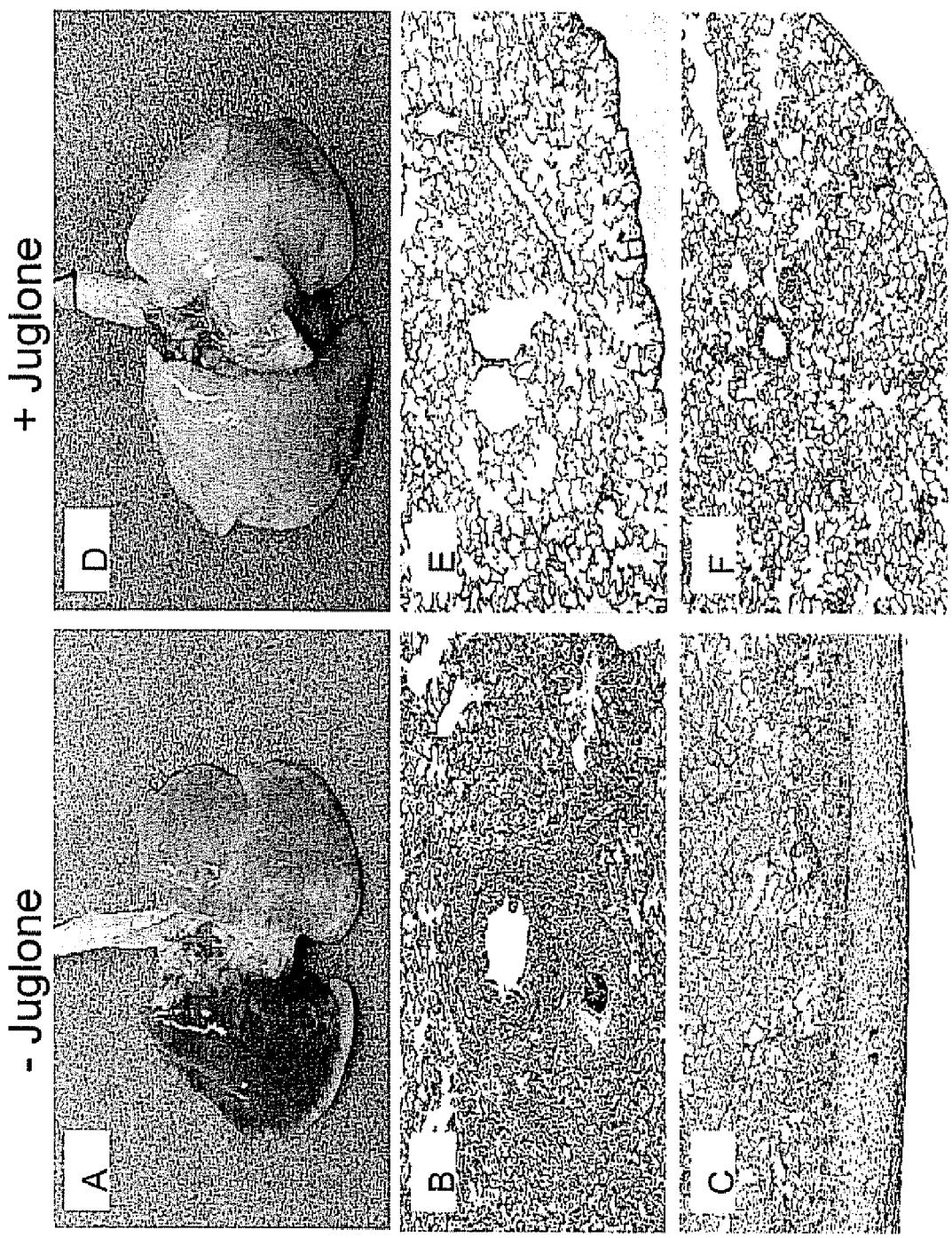
FIG. 19 shows that Pin1 is required for acute and chronic rejection.

Juglone was dissolved in ethanol and diluted in 5 ml saline. Control animals received ethanol only dissolved in 5 ml saline. Treatment was started the day of the transplant. At day 7 or 14, animals were sacrificed and the lungs evaluated grossly and by histopathology. In untreated animals, the transplant was visibly shrunken and the pleural surfaces hemorrhagic (FIG. 19A). Palpation revealed a firm and unyielding consistency. The juglone treated animals showed no gross signs of rejection (FIG. 19D) and the transplanted lungs were indistinguishable from the contralateral control. Microscopically, the untreated transplanted lung showed severe rejection with acute inflammatory cell infiltration predominantly composed of neutrophils, lymphocytes and macrophages. Alveolar architecture was totally effaced and the small airways packed with inflammatory cells (FIG. 19B). These changes were completely absent in juglone treated animals, which showed normal alveolar architecture, pleural thickness, and airway patency (FIG. 19E).

Occasional round macrophages were present in some alveoli. Identical data was been observed in 8 out of 10 treated animals. The two failures were early in this series and likely represented drug solubility problems. Analysis of the BAL fluid showed a significantly reduced number ($p<0.05$) of total cells present in the juglone treated compared to the control animals. No significant difference was found in the relative proportion of CD4, CD8 or γδ T cells in BAL fluid from the native right lung or in the transplanted left lung, which contrasted to collagen V tolerized animals that show predominantly CD4[+] T cells. These data demonstrated that Pin1 blockade dramatically attenuates acute transplant rejection.

Histopathologic analysis of untreated controls revealed alveolar, peribronchial and pleural collagen deposition (FIG. 19C). The alveolar spaces were full of fibrinoid material and there was complete loss of viable pneumocytes. The pleura was markedly fibrotic typically attaining over 20-fold its normal thickness with proliferating fibroblasts clearly visible. Juglone treated animals, however, showed minimal collagen deposition within the alveolar walls or around bronchi, the maintenance of viable pneumocytes and largely normal architecture (FIG. 19F). Therefore, Pin1 inhibition prevented collagen deposition and lung effacement comparable to that seen in chronic graft rejection.

Pin1 activity in BAL and mediastinal lymph node cells was examined at day 7 after transplant as follows. Activity was measured as described in Shen et al., 2005, *Nature Immunol* 12:1280-7). White blood cells from lymph node, spleen, and bronchoalveolar lavage fluid were lysed by repeated freeze-thaw cycles in a buffer containing 50 mM HEPES and 100 mM NaCl, pH 7.0. Total protein (10 μg in 10 μl) was mixed with 70 μl of HEPES-NaCl buffer supplemented with 2 mM dithiothreitol and 0.04 mg/ml BSA. Then, 5 μl of α-chymotrypsin (60 μg/μl in 0.001 N HCl) was added and mixed thoroughly. Finally, 5 μl of the tetrapeptide substrate Suc-Ala-Glu-Pro-Phe-pNa (SEQ ID NO: 1); Peptides International, Louisville, Ky.) dissolved in dimethylsulfoxide and preincubated at a concentration of 100 μg/ml in 480 mM LiCl and trifluoroethanol, was added. Absorption at 390 nm was measured over 30 min with a Beckman Coulter DU 800 spectrophotometer.

Figure 20A:
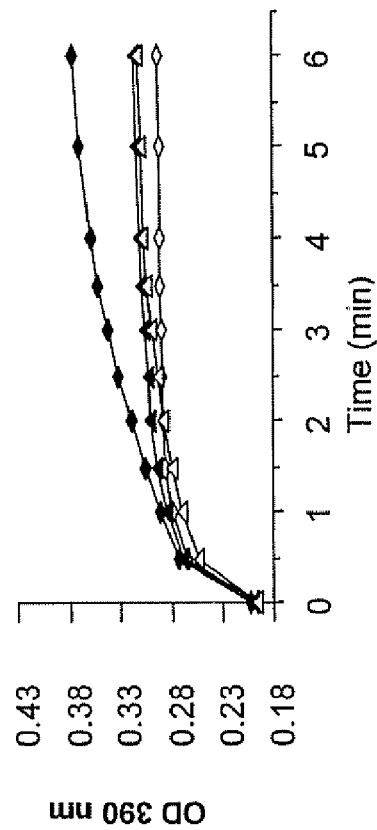
FIG. 20A shows a graph representing BAL fluid cells from untreated controls (♦), or juglone treated (▲) used for Pin1 isomerase assay. Juglone (1 µM) was also added in vitro to equal amounts of the control (◊) and juglone treated (△) samples and isomerase assay repeated.
Figure 20B:
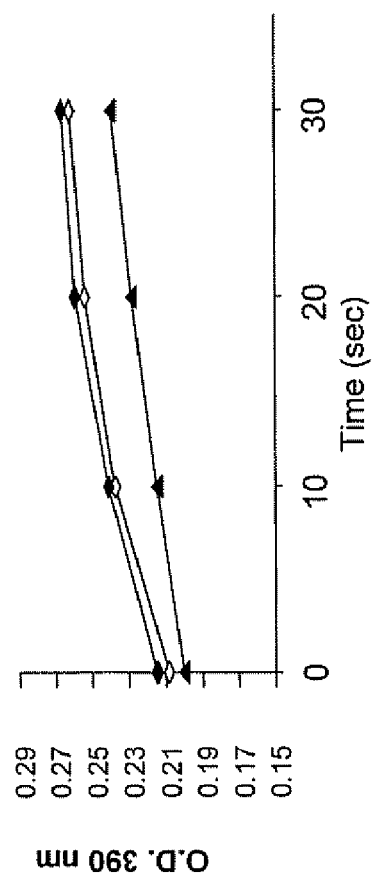
FIG. 20B shows a graph representing mediastinal lymph nodes from 2 untreated controls (♦, ◊) or one juglone treated animal (▲) used for Pin1 isomerase assay

After isomerization from cis to trans, the terminal 4-nitroanilide group can be cleaved by chymotrypsin and detected by absorbance at 390 nm. Pin1 activity in BAL cells from the transplanted left lung was significantly reduced in juglone treated rats (FIG. 20A). Addition of juglone to lysates of these cells had no further effect on Pin1 activity indicating maximal, in vivo suppression. Pin1 activity was significantly elevated in untreated, control BAL cells. Isomerase activity could be reduced in vitro to that seen in lysates from treated animals by the addition of juglone. Similarly, mediastinal lymph node cells from juglone treated animals displayed no Pin1 activity whereas control animals showed substantial elevations which again could be blocked by juglone in vitro (FIG. 20B). Therefore, MHC mismatched transplantation induced elevations in Pin1 activity in reactive immune cells. These changes can be prevented by in vivo administration of juglone.

Figure 20C:
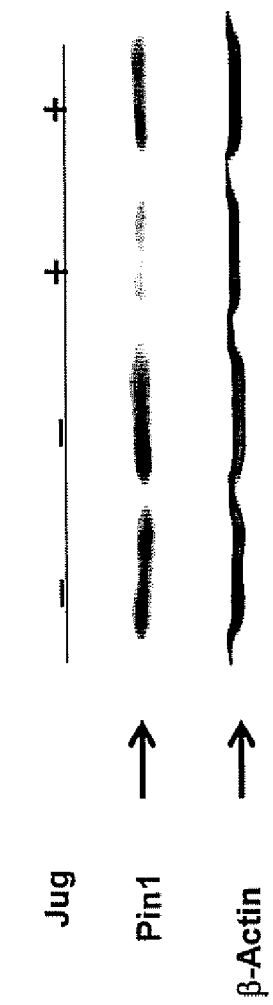
FIG. 20C shows an immunoblot with anti-Pin1 or anti-actin antibodies of mediastinal lymph nodes from control, untreated (−juglone) or juglone treated animals (+juglone).

Pin1 protein levels were analyzed in the mediastinal nodes of treated versus control animals by anti-Pin1 immunoblot analysis. As expected, juglone treated animals showed considerably reduced Pin1 protein in the mediastinal lymph nodes compared to the control animals (FIG. 20C). Pin1 levels and activity in the spleen of these same animals did not differ between control and juglone treated, suggesting compartmentalized immune responses, which were greatest in the most proximal nodes draining the mismatched transplant.

IFN-γ and CXCL-10 were Reduced After Pin1 Inhibition

Levels of IFN-γ and IL-2 were as measured, as described above, in the animals one week after transplantation. Analysis of the BAL fluid by ELISA showed highly significant reductions in IFN-γ (FIG. 21) and nearly significant reductions in IL-2 concentrations (FIG. 21). These data suggested that Pin1 block prevented cytokine production by T cells, which were the predominant population within the BAL fluid.

Figure 22A:
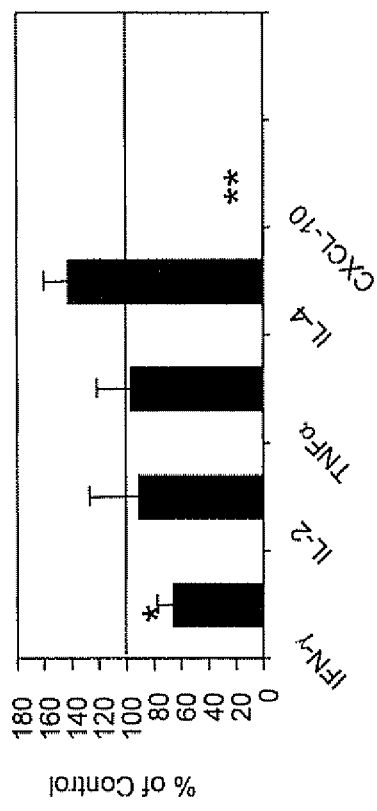
FIG. 22A shows a graph representing mediastinal lymph nodes from control or juglone treated used for reverse transcription, qPCR for the cytokines shown along the x-axis. The values in untreated controls were normalized to 100% and data shown represent % change in juglone treated samples. The data shown are an average±SEM (n=4 rats) of 4 experiments. * denotes p<0.05 from control samples.

Mediastinal lymph node cells were then analyzed for the expression of cytokine mRNAs by qPCR. mRNAs coding for IFN-γ, IL-2, CXCL-10, and TNF-α were significantly lower in juglone treated animals than controls whereas IL-4 and TGF-β1 were unaffected (FIG. 22A). These data suggested that Pin1 was involved in the regulation of a subset of cytokine mRNAs. Of note, IFN-γ, IL-2, CXCL-10 and TNF-α all contain 3' untranslated region (3' UTR) AREs, are rapidly degraded in resting cells, and show substantial, activation dependent stabilization. While IL-4 mRNA also contains AU-rich elements, it is typically highly expressed and relatively stable in resting cells. TGF-β1 mRNA lacks multiple AREs and typically decays slowly in resting cells.

To determine if TGF-β1 signaling in fibroblasts depends on Pin1, cultured lung fibroblasts were stimulated with TGF-β1. Primary lung fibroblasts were obtained from Clonetics (Cambrex BioScience, Baltimore, Md.) and cultured as described by the manufacturer. Passage 4 cells were grown to 80% confluence, transferred to serum deficient media for 48 h prior to stimulation with TGFβ (1 ng/ml) for 4 h with or without juglone. Cells were lysed and RNA isolated for RT-qPCR analysis of collagen III expression. As shown (FIG. 22D), stimulated fibroblasts showed substantial increases in collagen I and III mRNA, which were reduced in a dose dependent manner by increasing concentrations of juglone. Thus, despite elevated levels of TGF-β1, collagen production by lung fibroblasts was blocked by Pin1 inhibition.

Figure 22C:
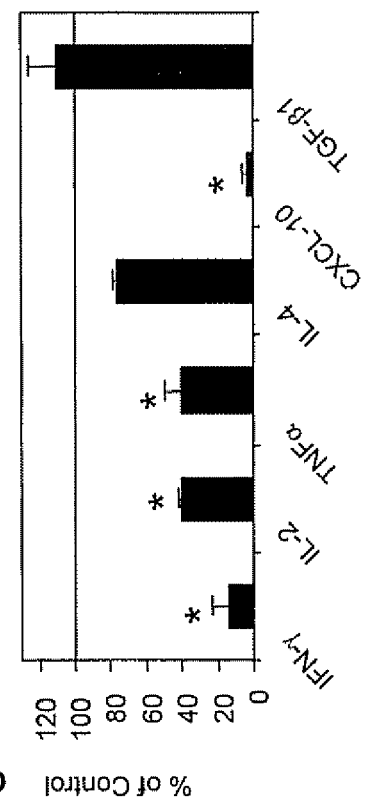
FIG. 22C shows a graph representing IFN-γ positive splenocytes quantitated by Elispot. * denotes p<0.05.
Figure 22B:
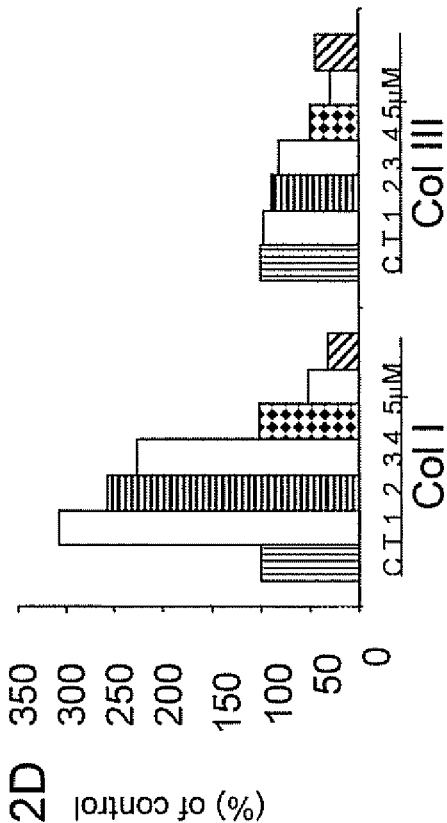
FIG. 22B shows a graph representing splenocytes used for qPCR as described for (FIG. 22A) above. * denotes p<0.05, ** denotes p<0011.
Figure 22D:
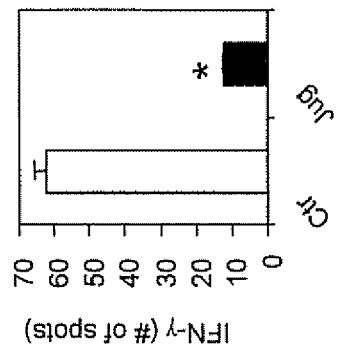
FIG. 22D shows a graph representing primary lung fibroblasts grown to 80% confluence, serum starved for 48 h prior to no stimulation (C), 1 ng/ml TGFβ1 (T) or TGFβ1 plus 1, 2, 3, 4 or 5 µM juglone (as shown) for 12 h prior to lysis, RNA isolation and collagen I or collagen III mRNA determination by qPCR. Values are normalized to control (100%).

Cytokine mRNAs from splenocytes in juglone treated animals were also examined. Based on ELISPOT (R&D Systems) used as described by the manufacturer, IFN-γ and IL-2 production by activated spleen cells were significantly reduced in the juglone treated animals (FIG. 22C). QPCR revealed that IFN-γ and CXCL-10 mRNA were significantly reduced whereas IL-2, TNF-α, and IL-4 mRNA expression were unchanged from controls (FIG. 22B). Therefore, Pin1 inhibition selectively reduced IFN-γ and CXCL-10 mRNA in the spleen, BAL and mediastinal nodes.

Overexpression of IFN-γ and CXCL-10 Overcame Pin1 Blockade and Induced Rejection The results shown in FIGS. 21 and 22 demonstrated that Pin1 was required for the induction of IFN-γ and CXCL-10 by activated mediastinal lymph node and BAL immune cells. In order to demonstrate a causal rather than associative role, IFN-γ and CXCL-10 expression vectors were combined and insufflated into donor lungs immediately before religature in the recipient. To avoid potential Pin1-mediated, post-transcriptional regulation, only the coding region without the 3' UTR was inserted downstream of a constitutively active CMV promoter. pcDNA1 (InVitrogen Corp., Carlsbad, Calif.) was opened at XbaI and XhoI sites and PCR products coding for the coding regions of IFN-γ and CXCL-10 inserted via sticky end ligation using standard methods. Putative clones were sequenced to ensure full length insert was present in the appropriate orientation. After amplification, plasmids were precipitated, washed and resuspended in sterile Tris-HCl/EDTA (TE) at 1 mg/ml and 100 μl used for insufflation.

Figure 23:
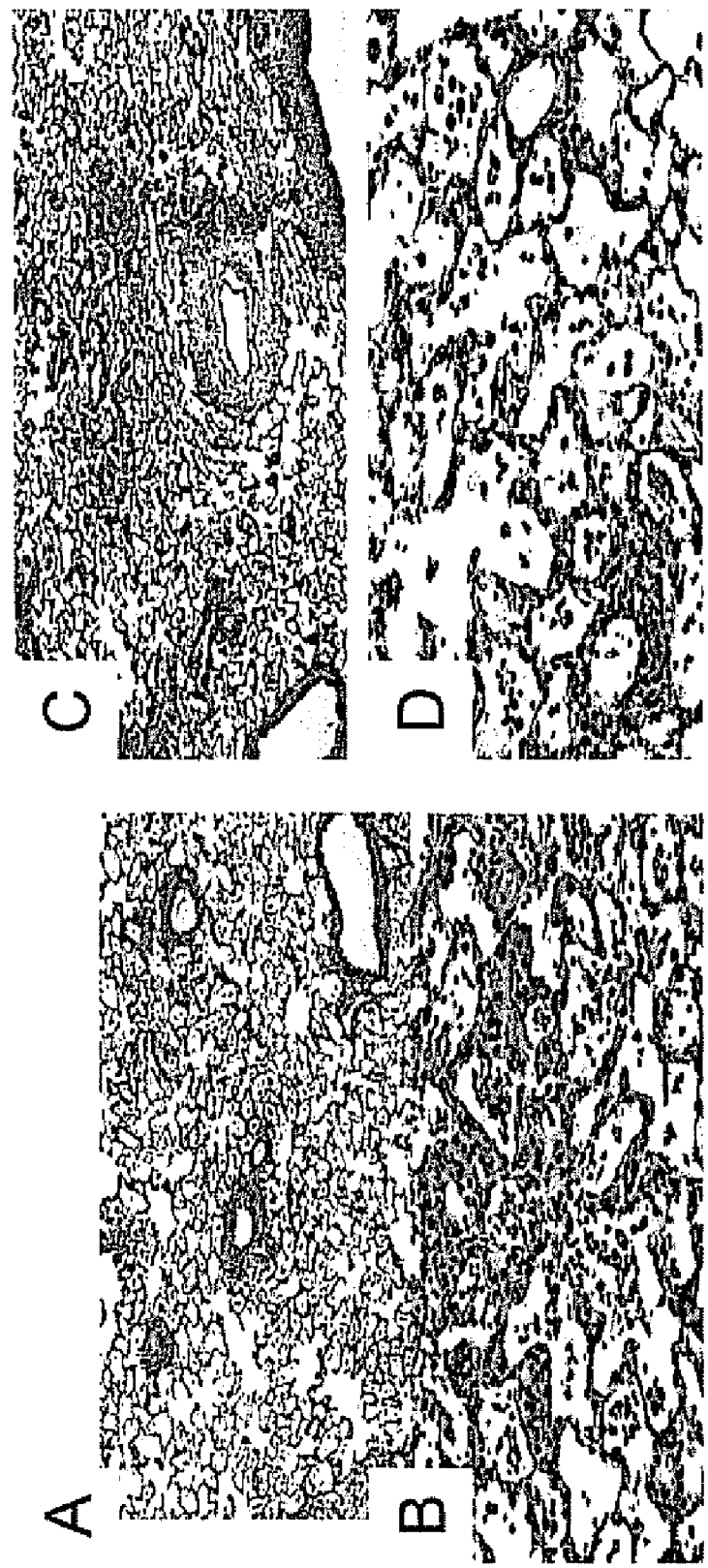
FIG. 23 shows that overexpression of CXCL-10 and IFNγ overcome Pin1 blockade. Donor lungs were insufflated with 100 µg each of CXCL-10 and IFNγ expression vectors immediately prior to religation in recipient. Animals were then untreated (FIG. 23A and FIG. 23B) or treated with juglone at 1 mg/kg for 1 week (FIG. 23C and FIG. 23D) as in FIG. 2 and histopathologic analysis after H & E staining. Representative sections from multiple animals are shown.

The effects of pulmonary IFN-γ and CXCL-10 expression on rejection were then examined. By 1 week after transplant, the lung grafts underwent profound rejection in untreated controls (FIGS. 19A, B), which was prevented by juglone (FIGS. 19B, D). The forced expression of IFN-γ and CXCL-10 resulted in severe cellular infiltration irrespective of Pin1 blockade (FIGS. 23A and B versus FIGS. 23C and D). Transgenic cytokines were detectable in the BAL at comparable levels to that seen in untreated recipients. These results supported a central role of IFN-γ and CXCL-10 in the process of acute rejection and suggested that cytokine suppression after Pin1 inhibition was partially responsible for graft sparing.

Juglone and CyclosporinA Showed Additive Effects

To determine if combined cyclosporine A (CsA) and juglone therapy would be additive or synergistic, the following experiment was conducted. Juglone was dissolved in 100% ethanol at 14 mM (2.44 mg/ml). For injection between 100 and 150 μl of this solution (depending on the animal weight) was diluted in 5 ml saline and injected intraperitoneally within 30 minutes. For suboptimal dosing between 10 and 25 μl of this solution was injected. Control animals received weight appropriate volume (100-150 μl; 10-25 μl resp.) of 100% ethanol in 5 ml saline. CsA was dissolved in 100% ethanol at 25 mg/ml. For injection 10 to 25 μl of this solution (depending on the animal weight) was diluted in 5 ml saline and injected prior to the transplantation and the two following days.

Figure 24:
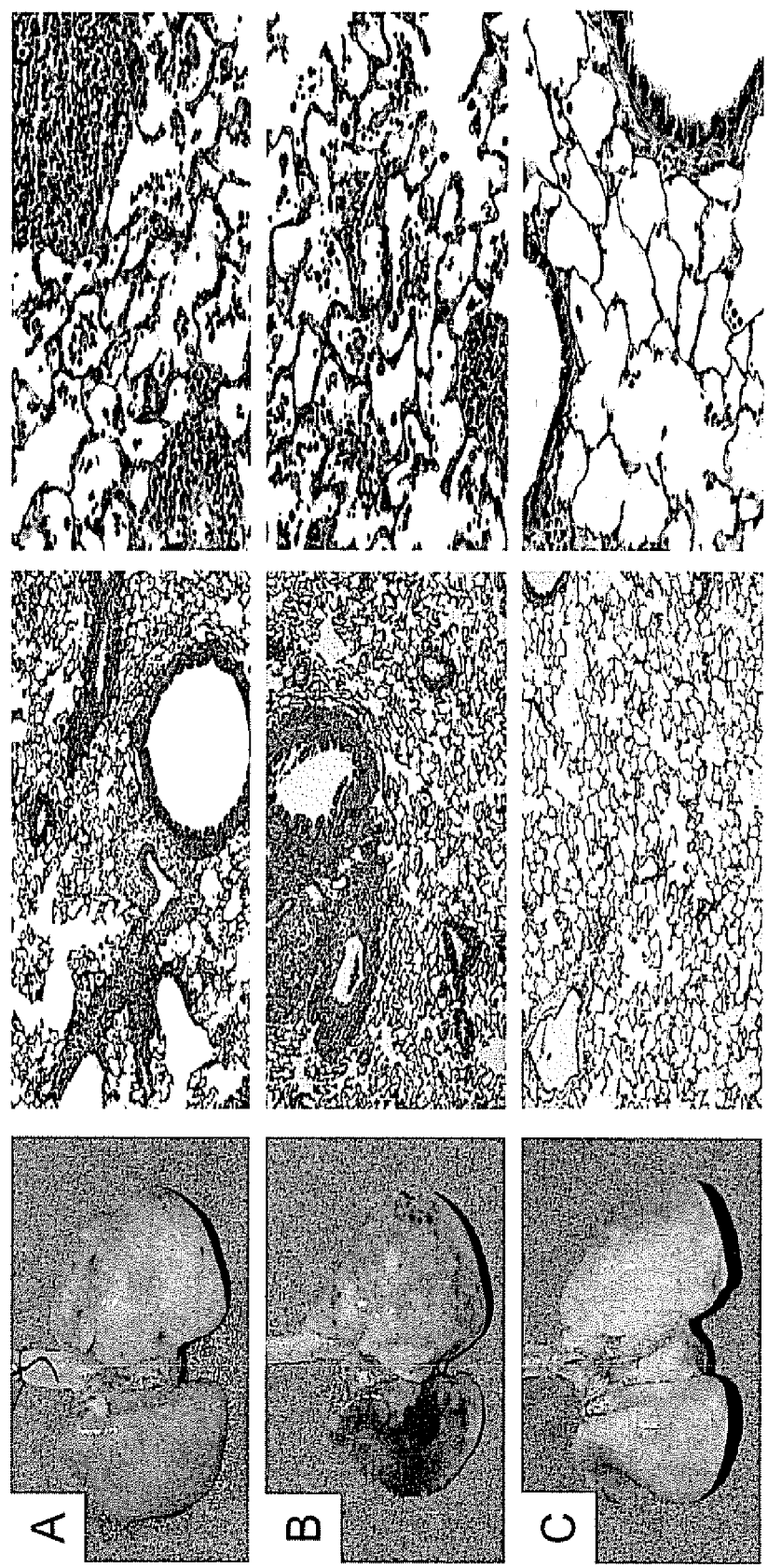
FIG. 24 shows that juglone and CsA are synergistic. Transplants were performed as described in FIG. 19 and animals harvested 7 days later.

CsA was injected intraperitoneally for 3 days at a dose of 1 mg/kg together with 0.1 mg/kg of juglone, which was then continued alone for 4 more days. Cyclosporine is usually used at 25 mg/kg/day for 3 days, which induces long lived lung transplant acceptance in rats while moderate to severe rejection was observed at doses of 5 mg/kg/d (Pierog et al., 2005, *Eur. J. Cardiothorac. Surg.* 27:1030-1035). Transplanted animals treated with CsA alone (1 mg/kg/d) showed modest graft discoloration (FIG. 24A), but microscopically severe cellular infiltration diffusely throughout the parenchyma with foci in peribronchial and perivascular areas (FIG. 24A). Similarly, suboptimal inhibition of Pin1 lead to severe rejection pathology with substantial cellular infiltration and hemorrhage (FIG. 24B). In contrast, combined suboptimal treatment with CsA and juglone provided excellent graft protection without identifiable cellular infiltrates (FIG. 24C). These data showed that combined inhibition of Pin1 and calcineurin were additive or synergistic and suggested that CsA dosage could be reduced when Pin1 inhibition was added to the therapeutic regiment.

It should be understood that the foregoing disclosure emphasizes certain specific embodiments of the invention and that all modifications or alternatives equivalent thereto are within the spirit and scope of the invention as set forth in the appended claims.

What is claimed is:

1. A method for inducing apoptosis in eosinophils comprising the step of contacting an eosinophil with a Pin1 inhibitor.

2. The method of claim 1, wherein the Pin1 inhibitor is a small molecule inhibitor.

3. The method of claim 1, wherein the Pin1 inhibitor is juglone.

* * * * *